US008476247B2

(12) United States Patent
Kim et al.

(10) Patent No.: US 8,476,247 B2
(45) Date of Patent: *Jul. 2, 2013

(54) METHOD OF REDUCING INTRAOCULAR PRESSURE IN HUMANS

(75) Inventors: Norman N. Kim, Westford, MA (US); William K. McVicar, Sudbury, MA (US); Thomas G. McCauley, Cambridge, MA (US); Prakash Jagtap, N. Andover, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/072,349

(22) Filed: Mar. 25, 2011

(65) Prior Publication Data
US 2011/0245195 A1 Oct. 6, 2011

Related U.S. Application Data

(60) Provisional application No. 61/318,105, filed on Mar. 26, 2010.

(51) Int. Cl.
*A61K 31/70* (2006.01)
*C07H 19/167* (2006.01)
*C07H 19/173* (2006.01)

(52) U.S. Cl.
USPC .......................................... 514/46; 536/27.62

(58) Field of Classification Search
None
See application file for complete search history.

(56) References Cited

U.S. PATENT DOCUMENTS

| 7,423,144 | B2 | 9/2008 | Jagtap et al. | |
|---|---|---|---|---|
| 7,732,424 | B2 * | 6/2010 | Jagtap et al. | 514/46 |
| 2009/0258836 | A1 * | 10/2009 | Civan et al. | 514/46 |
| 2011/0123622 | A1 * | 5/2011 | Avery et al. | 424/489 |
| 2011/0245193 | A1 * | 10/2011 | Kim et al. | 514/46 |

FOREIGN PATENT DOCUMENTS

| CN | 101010085 | 8/2007 |
|---|---|---|
| WO | 2007/064795 A2 | 6/2007 |
| WO | 2010/127210 A1 | 11/2010 |

OTHER PUBLICATIONS (R) Karl et al., "Differential P1-Purinergic Modulation of Schlemm's Canal Inter-Wall Cells," Am. J. of Physiology, Cell Physiology, 288(4), C784-C794 (2005).*
Accession No. 1994:153455, Higuchi, T. et al., "Evaluation of Serum Lactate-Dehydrogenase Activity for Estimation of Energy-Expenditure in Human-Subjects," Ergonomics, vol. 37(3):389-397 (1994).
Accession No. 2001:494425, Martin, H. et al., "The Guardian/Observer: Information developments since 1998," Aslib Proceedings, vol. 53(5):161-166 (2001).
Accession No. 2002:660483, Shore, G.M. et al., "eta '(eta)->gamma gamma: A tale of two anomalies," Physica Scripta, vol. T99:84-95 (2002).
Accession No. 2004:827690, Tacke, R. et al., "Sila-haloperidol: a silicon analogue of the dopamine (D-2) receptor antagonist haloperidol," Organometallics, vol. 23(19):4468-4477 (2004).
Avila, Marcel Y. et al., "A1-, A2A- and A3-subtype adenosine receptors modulate intraocular pressure in the mouse," British Journal of Pharmacology, vol. 134:241-245 (2001).
ACS Registry No. 365533-73-9 (2001).
ACS Registry No. 151563-23-4 (1993).
ACS Registry No. 365533-72-8 (2001).
ACS Registry No. 365533-74-0 (2001).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E. et al., "Characterization of Ocular Hypertension Induced by Adenosine Agonists," Investigative Ophthalmology & Visual Science, vol. 37(9):1833-1839 (1996).
Crosson, Craig E. et al., "Modulation of Intraocular Pressure by Adenosine Agonists," Journal of Ocular Pharmacology, vol. 10(1):379-383 (1994).
Dalpiaz, Alessandro et al., "Development and characterization of biodegradable nanospheres as delivery systems of anti-ischemic adenosine derivatives," Biomaterials, vol. 26:1299-1306 (2005).
Dalpiaz, Alessandro et al., "Fabrication Via a Nonaqueous Nanoprecipitation Method, Characterization and In Vitro Biological Behavior of N6-Cyclopentyladenosine-Loaded Nanoparticles," Journal of Pharmaceutical Sciences, vol. 98 (11):4272-4284 (2009).
Dalpiaz, Alessandro et al., "Synthesis and Study of 5'-Ester Prodrugs of N6-Cyclopentyladenosine, a Selective A1 Receptor Agonist," Pharmaceutical Research, vol. 18(4):531-536 (2001).
Fleischhauer, J.C. et al., "Common Actions of Adenosine Receptor Agonists in Modulating Human Trabecular Meshwork Cell Transport," J. Membrane Biol., vol. 193:121-136 (2003).
Fleisher, David et al., "Improved oral drug delivery: solubility limitations overcome by the use of prodrugs," Advanced Drug Delivery Reviews, vol. 19:115-130 (1996).
Fredholm, Bertil B. et al., "International Union of Pharmacology. XXV. Nomenclature and Classification of Adenosine Receptors," Pharmacological Reviews, vol. 53(4):527-552 (2001).
Hirao, Mami et al., "Effects of adenosine on optic nerve head circulation in rabbits," Experimental Eye Research, vol. 79:729-735 (2004).
Husain, S. et al., "Mechanisms Linking Adenosine A1 Receptors and Extracellular Signal-Regulated Kinase ½ Activation in Human Trabecular Meshwork Cells," The Journal of Pharmacology and Experimental Therapeutics, vol. 320(1):258-265 (2007).

(Continued)

*Primary Examiner* — Lawrence E Crane
(74) *Attorney, Agent, or Firm* — Nelson Mullins Riley & Scarborough LLP; Jane E. Remillard, Esq.; Cynthia L. Kanik

(57) ABSTRACT

Provided herein is a method of reducing intraocular pressure (IOP) in humans using N6-cyclopentyladenosine (CPA), CPA derivatives or prodrugs or enhanced cornea permeability formulations of CPA. In one embodiment, the invention is directed to CPA derivatives or prodrugs that are permeable to the cornea. In another embodiment, the invention is directed to uses of certain compounds in human subjects for reducing and/or controlling elevated or abnormally fluctuating IOPs in the treatment of glaucoma or ocular hypertension (OHT).

19 Claims, 5 Drawing Sheets

OTHER PUBLICATIONS

Konno, Takashi et al., "2-(1-Hexyn-1-yl)adenosine-induced intraocular hypertension is mediated via K+ channel opening through adenosine A2A receptor in rabbits," European Journal of Pharmacology, vol. 518:203-211 (2005).

Konno, Takashi et al., "Effect of chymase on intraocular pressure in rabbits," European Journal of Pharmacology, vol. 524:132-137 (2005).

Konno, Takashi et al., "Involvement of Adenosine A2a Receptor in Intraocular Pressure Decrease Induced by 2-(1-Octyn-1-yl)adenosine or 2-(6-Cyano-1-hexyn-1-yl)adenosine," J. Pharmacol. Sci., vol. 97:501-509 (2005).

Maillard, Michel C. et al., "Adenosine Receptor Prodrugs: Synthesis and Biological Activity of Derivatives of Potent, A1-Selective Agonists," Journal of Pharmaceutical Sciences, vol. 83(1):46-53 (1994).

Ralevic, Vera et al., "Receptors for Purines and Pyrimidines," Pharmacological Reviews, vol. 50(3):413-492 (1998).

Robinson, Ralph P. et al., "Discovery of the Humifumarate and (alpha-L-Alanyloxy)methyl Ether as Prodrugs of an Antirheumatic Oxindole: Prodrugs for the Enolic OH Group," J. Med. Chem., vol. 39:10-18 (1996).

Tian, Baohe et al., "Effects of Adenosine Agonists on Intraocular Pressure and Aqueous Humor Dynamics in Cynomolgus Monkeys," Exp. Eye Res., vol. 64:979-989 (1997).

Tsilimbaris, Miltiadis K. et al., "The Use of Atomic Force Microscopy for the Observation of Corneal Epithelium Surface," Invest. Ophthalmol. Vis. Sci., vol. 41:680-686 (2000).

International Search Report for Application No. PCT/US2011/030009, dated Jun. 17, 2011.

Chinese Office Action for Application No. 201080018539.X, 9 pages, dated Nov. 2, 2012.

* cited by examiner

METHOD OF REDUCING INTRAOCULAR PRESSURE IN HUMANS

CROSS-REFERENCE TO RELATED APPLICATIONS

This application claims priority to U.S. Provisional Application No. 61/318,105, filed Mar. 26, 2010. The entire contents of the aforementioned application and any patents, patent applications, and references cited throughout this specification are herein incorporated by reference in their entireties.

TECHNICAL FIELD OF THE INVENTION

Provided herein is a method of reducing intraocular pressure (IOP) in humans using N6-cyclopentyladenosine (CPA), CPA derivatives or prodrugs, or enhanced cornea permeability formulations of CPA. In one embodiment, the invention is directed to CPA derivatives or prodrugs that are cornea-permeable. In another embodiment, the invention is directed to uses of CPA compounds in human subjects for reducing and/or controlling elevated or abnormally fluctuating IOPs in the treatment of glaucoma or ocular hypertension (OHT). Cyclopentyladenosine—$N^6$-cyclopentyladenosine

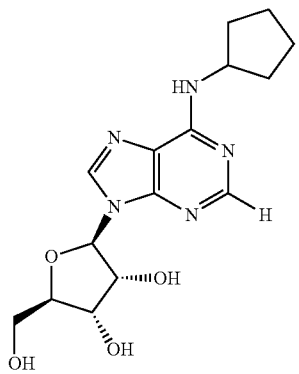

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated IOP is a major risk factor for glaucoma and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

OHT is a condition in which IOP is elevated but no glaucomatous findings have been observed (Bell, 2005). The Ocular Hypertension Study demonstrated that patients with OHT have an overall risk of 10% over 5 years of developing glaucoma and that this risk can be cut in half by the institution of medical treatment that reduces IOP.

Drug therapies that have proven to be effective for the reduction of intraocular pressure include both agents that decrease aqueous humor production and agents that increase the outflow facility. Such therapies are in general administered by one of two possible routes: topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes, irises, and periorbital tissues. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies.

Therefore, there remains a need for new treatments and therapies for elevated intraocular pressure (IOP), and conditions caused by elevated IOP. There is also a need for compounds useful in the treatment or prevention or amelioration of one or more symptoms of elevated IOP and conditions caused by elevated IOP.

SUMMARY OF THE INVENTION

There remains a need for new treatments and therapies for elevated intraocular pressure (IOP), and conditions caused by elevated IOP. There is also a need for compounds useful in the treatment or prevention or amelioration of one or more symptoms of elevated IOP and conditions caused by elevated IOP.

In a first aspect, the present invention provides a method of reducing intraocular pressure comprising the step of: delivering an effective amount of cyclopentyladenosine according to Formula I to the anterior chamber of an affected eye of a human,

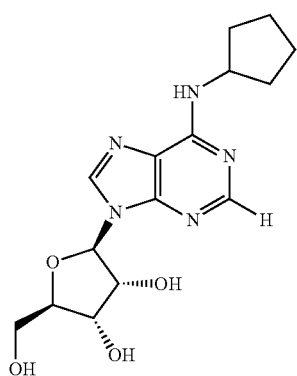

(I)

with the proviso that the compound of Formula I is not delivered in the form of compound A

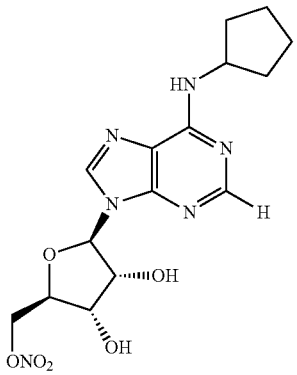

((2R,3S,4R,5R)-5-(6-(cyclopentylamino)-9H-purin-9-yl)-3,4-dihydroxytetrahydrofuran-2-yl)methyl nitrate.

In another aspect the method as defined above further comprises the prior, simultaneous or sequential, application of a second IOP reducing agent. In one embodiment the second IOP reducing agent is selected from the group comprising: β-blockers, prostaglandin analog, prostamides, carbonic anhydrase inhibitors, rho-kinase inhibitors, α₂ agonists, miotics, neuroprotectants, $A_1$ agonist, $A_3$ antagonists, $A_2A$ agonists and combinations thereof.

In yet another aspect, the present invention provides a method of reducing intraocular pressure comprising the step of: delivering an effective amount of cyclopentyladenosine according to Formula I in a cornea-permeable form to the anterior chamber of an affected eye of a human,

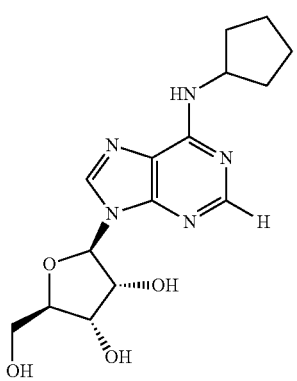

or a pharmaceutically acceptable salt thereof,
with the proviso that the compound of Formula I is not delivered in the form of compound A

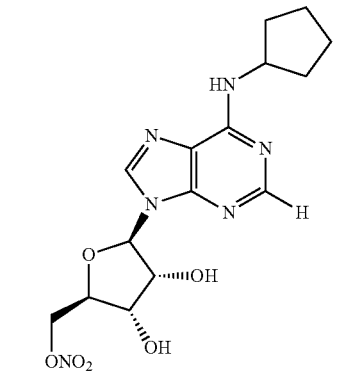

((2R,3S,4R,5R)-5-(6-(cyclopentylamino)-9H-purin-9-yl)-3,4-dihydroxytetrahydrofuran-2-yl)methyl nitrate.

In another aspect the method as defined above further comprises the prior, simultaneous or sequential, application of a second IOP reducing agent. In one embodiment the second IOP reducing agent is selected from the group comprising: β-blockers, prostaglandin analog, prostamides, carbonic anhydrase inhibitors, rho-kinase inhibitors, α₂ agonists, miotics, neuroprotectants, $A_1$ agonists, $A_3$ antagonists, $A_2A$ agonists and combinations thereof.

In another aspect the present invention is directed to a compound of Formula II,

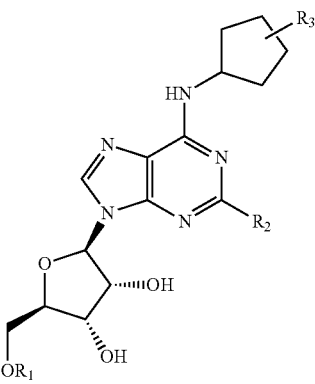

or a pharmaceutically acceptable salt thereof,
wherein $R_1$ is selected from —(CO)$C_1$-$C_6$ alkyl, —(CO)CH(halo)$_2$, —(CO)phenyl, or a —CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6; —(CO)aryl which is optionally substituted with one or more of hydroxy or —(CH$_2$)$_n$OH where n is 1-6; or a —(CO)$C_3$-$C_7$ heterocyclic which is optionally substituted with one or more of hydroxy or —(CH$_2$)$_n$OH, where n is 1-6; $R_2$ is selected from —H or halo; and $R_3$ is selected from —H, hydroxy, —O(CO)CH(halo)$_2$, —O(CO)(CH$_2$)$_2$CH$_3$, —O(CO)CH(CH$_3$)$_2$, —O(CO)CH$_2$C(CH$_3$)$_3$.

In still another aspect the invention is directed to a method of reducing IOP and associated diseases and conditions caused by elevated IOP in a human subject by administering an effective amount of a compound of Formula II to an affected eye of the human subject,

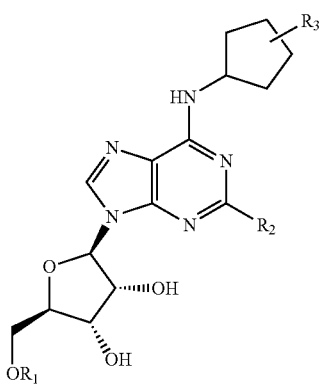

(II)

or a pharmaceutically acceptable salt thereof,
wherein $R_1$ is selected from —(CO)$C_1$-$C_6$ alkyl, —(CO)CH(halo)$_2$, —(CO)phenyl, or a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; or a —(CO)$C_3$-$C_7$ heterocyclic which is optionally substituted with one or more of hydroxy or —(CH$_2$)$_n$OH where n is 1-6; $R_2$ is selected from —H or halo; and $R_3$ is selected from —H, hydroxy, —O(CO)CH(halo)$_2$, —O(CO)(CH$_2$)$_2$CH$_3$, —O(CO)CH(CH$_3$)$_2$, —O(CO)CH$_2$C(CH$_3$)$_3$.

In one embodiment the diseases and conditions caused by elevated IOP in a human are selected from the group consisting of normal-tension glaucoma, OHT, and POAG.

In one embodiment the method comprises the step of applying about 0.05 mg/ml to about 7.0 mg/ml of a compound according to Formula II from 1 to 4 times daily, or in another embodiment the method comprises the step of applying about 20-700 μg of a compound according to Formula II from 1 to 2 times daily or in another embodiment the method comprises the step of applying about 350 μg of a compound according to Formula II from 1 to 2 times daily.

In one embodiment the IOP of the affected eye is reduced by at least 10%. In another embodiment the IOP of the affected eye is reduced by at least 10-20%. In a further embodiment the IOP of the affected eye is reduced by 20% or more.

In one embodiment the IOP of the affected eye is reduced by at least 10% for more than 3 hours, in another embodiment the IOP of the affected eye is reduced by at least 10-20% for more than 3 hours, in a further embodiment the IOP of the affected eye is reduced by 20% or more for more than 3 hours and in another embodiment the IOP of the affected eye is reduced by at least 10% for at least 6 hours.

In another aspect the method as defined above further comprises the prior, simultaneous or sequential, application of a second IOP reducing agent. In one embodiment the second IOP reducing agent is selected from the group comprising: β-blockers, prostaglandin analog, prostamides, carbonic anhydrase inhibitors, rho-kinase inhibitors, $α_2$ agonists, miotics, neuroprotectants, ion channel modulators, $A_1$ agonists, $A_3$ antagonists, $A_2A$ agonists and combinations thereof.

In one embodiment the effective amount of the compound of Formula II is at least 20 μg.

In one embodiment the effective amount of the compound of Formula II is between 60 μg and 700 μg.

In one embodiment the effective amount of the compound of Formula II is administered as a single dose.

In one embodiment the effective amount of the compound of Formula II is administered as a twice daily dose.

In another aspect there is provided an ophthalmic pharmaceutical composition comprising a compound of Formula II as defined above and a pharmaceutically acceptable vehicle or excipient.

In one embodiment the pharmaceutically acceptable vehicle or excipient is selected from the group comprising of: ophthalmologically acceptable preservatives, surfactants, viscosity enhancers, penetration enhancers, gelling agents, hydrophobic bases, vehicles, buffers, sodium chloride, and water.

In one embodiment the composition further comprises a second IOP reducing agent in addition to a compound of Formula I as defined above. The second IOP reducing agent is selected from the group comprising: β-blockers, prostaglandin analogs, prostamides, carbonic anhydrase inhibitors, rho-kinase inhibitors, $α_2$ agonists, miotics, neuroprotectants, ion channel modulators, $A_1$ agonists, $A_3$ antagonists, $A_2A$ agonists and combinations thereof.

In another aspect there is provided a compound of Formula III

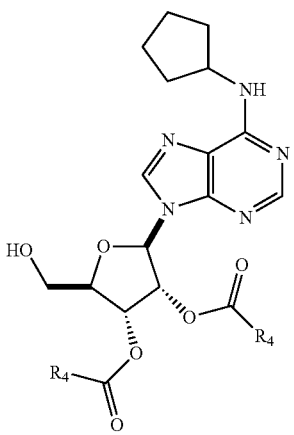

(III)

wherein $R_4$ is selected from —CH$_3$, —CH(CH$_3$)$_2$, —CH(halo)$_2$, —CH$_2$C(CH$_3$)$_3$, —CH$_2$CH(CH$_3$)$_2$, —C(CH$_3$)$_3$, —(CH$_2$)$_2$CH$_3$, —(CH$_2$)$_3$CH$_3$, —(CH$_2$)$_4$—CH$_3$, —(CH$_2$)$_5$CH$_3$, —(CH$_2$)$_6$CH$_3$, —CH$_2$CH$_3$, -phenyl, or -benzyl.

In a further aspect CPA or a prodrug of CPA such as that of Formula II or Formula III can be used to lower and/or control IOP associated with normal-tension glaucoma, OHT, and POAG in humans. In certain embodiments, when used to treat normal-tension glaucoma or OHT, the compounds of Formula II can be formulated in pharmaceutically acceptable compositions suitable for topical delivery to the eye.

Another embodiment of the present invention comprises an ophthalmic pharmaceutical composition useful in the reduction of intraocular pressure, comprising an effective amount of a compound according to Formula II.

It is to be further appreciated that the use of a compound of CPA or of Formula II as defined above, or ophthalmic compositions as defined above may be used for manufacture of a medicament for reducing IOP in an affected eye of a human subject.

It is recognized that compounds of Formula I, II or Formula III can contain one or more chiral centers. This invention contemplates all enantiomers, diastereomers, and mixtures of Formulas I, II and III thereof.

Furthermore, certain embodiments of the present invention comprise pharmaceutically acceptable salts of compounds according to Formula I, II or III.

Pharmaceutically acceptable salts comprise, but are not limited to, soluble or dispersible forms of compounds according to Formula I, II or III that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
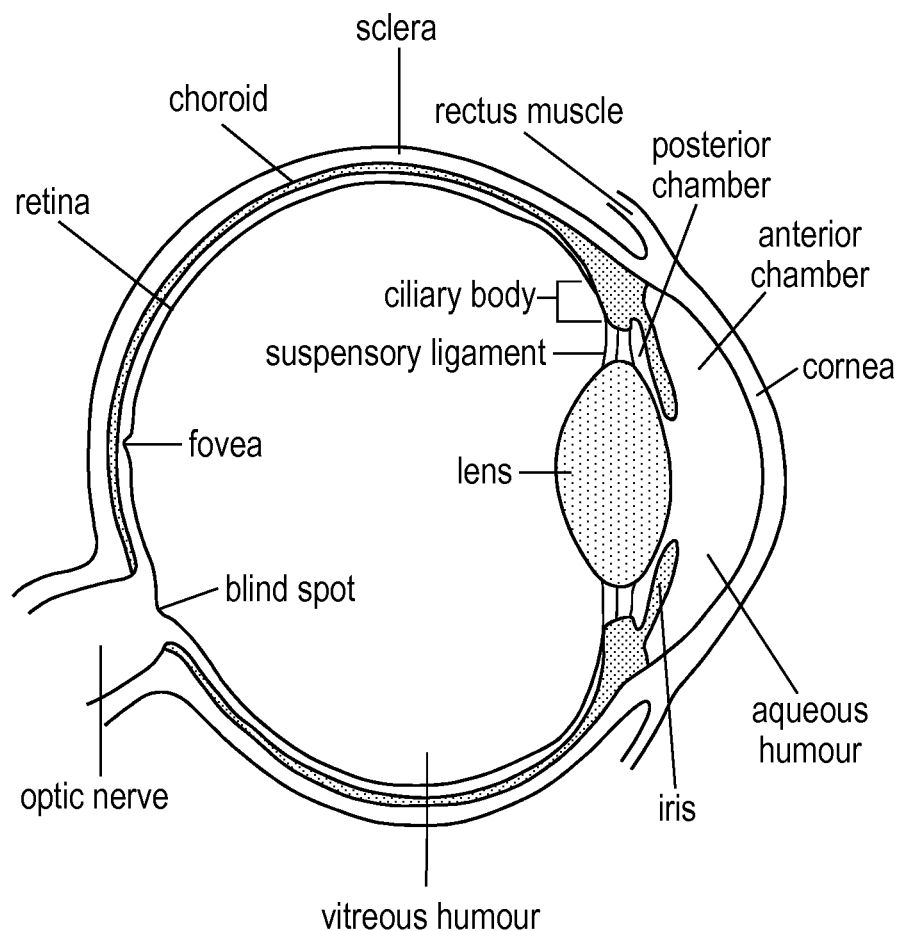
FIG. 1: shows a cross section diagram of a human eyeball and shows the relationship of the cornea to the anterior chamber.

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

DEFINITIONS

The term "cornea permeability" as used herein refers to the percentage of active compound delivered to the anterior chamber relative to the percentage of a prodrug or active compound that is delivered topically to the cornea in an ocular eye drop (30-50 μl) for human cornea.

The term "$C_1$-$C_{10}$ optionally branched aliphatic" as used herein refers to a straight or branched chain; optionally unsaturated hydrocarbon having from 1 to 10 carbon atoms. Representative $C_1$-$C_{10}$ aliphatic groups include, but are not limited to ethylene, isopropylene, propyne, butyne, sec-butylene, pentylene, hexyldiene, heptylene, heptyne, octylene, octyne.

The term "aryl" as used herein refers to a phenyl group or a naphthyl group. In one embodiment, the aryl group is substituted with one or more of the following groups: —OH or OH—$C_1$-$C_6$alkyl groups. Unless indicated, the aryl is unsubstituted. The term "$C_3$-$C_8$ cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl, cyclooctyl and norbornyl. In one embodiment, the $C_3$-$C_8$ monocyclic cycloalkyl group is substituted with one or more of the following groups: OH or OH—$C_1$-$C_6$alkyl groups. Unless indicated, the $C_3$-$C_8$ monocyclic cycloalkyl is unsubstituted.

The term "effective amount" as used herein refers to an amount of a CPA or a CPA prodrug that is effective for: (i) treating or preventing elevated IOP; or (ii) reducing IOP in a human.

The term "halo" as used herein refers to —F, —Cl, —Br or —I.

The term "$C_3$- to $C_7$-heterocyclic" refers to: (i) a 3- or 4-carbon membered non-aromatic monocyclic cycloalkyl in which 1 of the ring carbon atoms has been replaced with an N, O or S atom; or (ii) a 5-, 6-, or 7-carbon membered aromatic or non-aromatic monocyclic cycloalkyl in which 1-4 of the ring carbon atoms have been independently replaced with a N, O or S atom. The non-aromatic 3- to 7-carbon membered monocyclic heterocycles can be attached via a ring nitrogen, sulfur, or carbon atom. The aromatic 3- to 7-carbon membered monocyclic heterocycles are attached via a ring carbon atom. Representative examples of a $C_3$- to $C_7$-membered heterocyclic group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl. In one embodiment, the $C_3$- to $C_7$-membered heterocyclics substituted with one or more of the following groups: OH or OH—$C_1$-$C_6$alkyl groups. Unless indicated, the 3- to 7-membered monocyclic heterocycle is unsubstituted.

The phrase "pharmaceutically acceptable salt," as used herein, is a salt of an acid and a basic nitrogen atom of a purine compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound. Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

The following abbreviations are used herein and have the indicated definitions: CPA is N6-cyclopentyladenosine; NMR is nuclear magnetic resonance; OHT is ocular hypertension or POAG is primary open-angle glaucoma.

The effects of CPA at lowering IOP have been previously reported in animal models. However, the results reported are mixed.

In 1994, Crosson and Gray reported in the *J. of Ocular Pharm. and Therapeutics*. 10(1) 379-383 that the administration of CPA (165 µg) resulted in a reduction of rabbit IOP.

In 2001, Avila et al., reported in *Brit. Journal of Pharmacology*, (2001) 134, 241-245, that the mouse is potentially a powerful vehicle for studying pharmacology of aqueous humor dynamics, particularly in view of the increasing availability of knockout animals. In their studies Avila et al. topically applied CPA using DMSO to the study eye of the mouse. They reported that the $A_1$ agonist CPA at 100 nm in three mice produced a change in IOP of −6.8 mm Hg (±1.8) while CPA at 1 mM in three mice produced a change in IOP of −1.0 mm Hg (±2.3). Avila. et al. suggested that at increased concentrations CPA did not lower IOP because of a negative oculotensive effect of the A1 receptor offset by the opposing effects of the $A_3$ and possibly $A_{2A}$ receptors.

In 2003 Fleischhauer et al. reported results of a study in the *J. of Membrane Biol.* (193, 121-36) where CPA was used to stimulate $A_1$ adenosine receptors in isolated human trabecular meshwork (TM) cells. The trabecular meshwork is an area of ocular tissue located around the base of the cornea, and is responsible for draining the aqueous humor from the eye via the anterior chamber (the chamber on the front of the eye covered by the cornea).

The authors concluded that the trabecular meshwork cells express functional $A_1$, $A_{2A}$ and $A_3$ receptors and that the enhancement of aqueous humor outflow by $A_1$ adenosine receptor agonists, such as CPA may possibly be mediated by reduction of TM cell volume.

In 2004 Hirao et al. reported in *Experimental Eye Research* 79, 729-735 the results of studies that suggest that CPA at a concentration of 10 nmol increased the optic nerve head tissue blood flow in rabbits after CPA was injected intravitreally. The results also suggest that adenosine increases the capillary blood flow in the optic nerve head of rabbits, and it acts through the $A_1$ and $A_{2a}$ receptors from the ablumenal side where pericytes are located.

In 2009, Dalpiaz et al. in *Journal of Pharmaceutical Sciences*, pages 1-13 reported the preparation of a nanoparticle loaded with CPA. The CPA loaded nanoparticle was tested under in-vitro conditions and found to penetrate the cellular membrane of human retinal pigment endothelium cells. As the authors describe in this paper, the clinical use of CPA is hampered by several aspects, including the fact that CPA is greatly unstable in physiological fluids along with the potential for indiscriminate activity because of the fact that adenosine receptors are ubiquitous in the body.

The inventors have also identified a number of CPA ester prodrugs that deliver CPA through the cornea. While some CPA esters have been previously identified by Dalpiaz et al. in *Pharmaceutical Research*, Vol. 18, No. 4, 2001 as being suitable as CPA prodrugs, there is no suggestion that such prodrugs could be topically delivered onto the cornea so as to deliver CPA to the anterior chamber of a human subject as a means of lowering the subject's IOP.

Traditional techniques of delivering CPA across the cornea of animals have used dimethylsulfoxide (DMSO) as the carrier of CPA, however, it is thought that the DMSO has probably masked the impermeability of CPA because it is likely that DMSO disrupts the cornea and CPA is delivered across the cornea as a result of the disruption to the cornea. DMSO is not a safe or suitable ocular solvent for human ocular drug delivery.

Surprisingly the inventors have found that the topical ocular administration of compound A

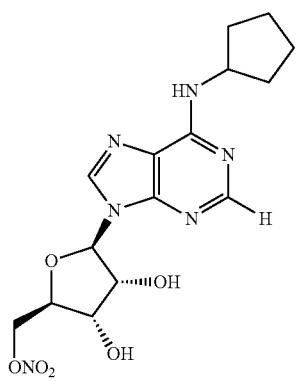

A in humans in a clinical trial resulted in the detection of CPA as an active metabolite in conjunction with Compound A to lower IOP in humans. Co-pending applications U.S. Ser. No. 61/174,655 and U.S. Ser. No. 61/219,990 teach the use of compound A in clinical trials to lower IOP in humans. The disclosures of U.S. Ser. No. 61/174,655 and U.S. Ser. No. 61/219,990 are incorporated herein in their entirety.

The inventors have surprisingly found that CPA does not have sufficient cornea permeability to allow the topical delivery of safe levels of CPA to the cornea of a human subject. Furthermore, the inventors have additionally found that if an effective amount of CPA can be safely delivered across the cornea of a human subject the subject's IOP can be significantly reduced.

Embodiments of the present invention provide the use of CPA or CPA prodrugs for treating reducing and controlling normal or elevated intraocular pressure (IOP) and/or treating glaucoma in human subjects.

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al. (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J. Pharmacol. 134:241-245, 2001). While other publications have noted that adenosine A1 receptor agonists in the eye target the conventional outflow pathway via the trabecular meshwork (Husain S et al. J Pharmacol Exp Ther. 320: 258-265, 2007), reduction of IOP via other pathways has not been excluded.

It should be noted that the highly robust, adenosine $A_1$ receptor-mediated drop in IOP reported in preclinical studies is often preceded by an immediate, yet transient elevation in IOP following instillation of the A1 receptor ligand (Crosson C E and Grey T. Inv Ophthal Visual Sci. 37, [9] 1833-1839, 1996). Transient elevations in IOP of ~3-9 mmHg have been observed in a ~30 min "window" after dosing. This phenomenon may arise from cross-reactivity between adenosine receptor sub-types within the eye. Pharmacological studies indicate that this transient elevation in IOP might be due, at least in part, to the activation of adenosine $A_{2B}$ receptors (Crosson, 1996). Therefore, development of a highly-selective A1 agonist that only reduce IOP would appear to be more tenable than the development of adenosine A2-receptor-based drugs for treating IOP, as A2A agonists may increase, decrease or exert mixed effects on IOP (Konno, 2004; Konno, J Pharmacol Sci., 2005; Konno, Eur J. Pharmacol. 2005).

Compounds that act as selective adenosine A1 agonists are known and have shown a variety of utilities. U.S. Pat. No. 7,423,144 to Jagtap et al. describes such selective adenosine A1 agonists compounds for the prevention or treatment of tachyarrhythmias (elevated heart rate), pain disorders, and ischemia-reperfusion injury.

Figure 2:
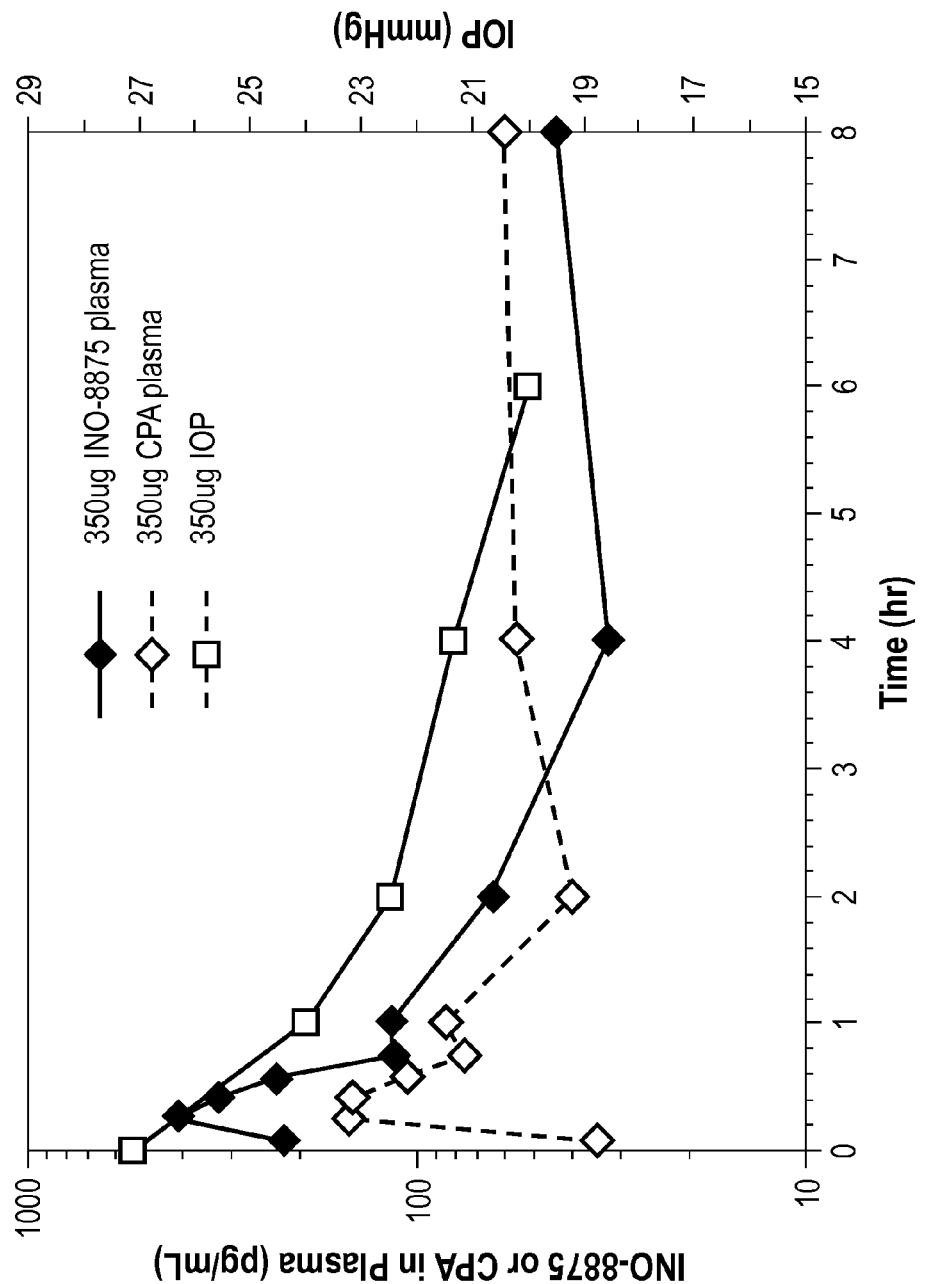
FIG. 2: shows the CPA levels and Compound A levels detected in the plasma of a human subject after the time of administration of 350 μg of Compound A topically to the cornea of the human subject relative to the IOP measured in the subject.

It has now been found that CPA has been identified as an active metabolite in clinical studies after the topical administration of Compound A to the cornea of human subjects. The IOP of the human subjects continues to decline after the buildup of CPA in the plasma of the human subjects and that no transient elevation in IOP is seen suggesting that the selectivity of CPA over the $A_2$ and $A_3$ adenosine receptors is significant enough to avoid any transient increase in IOP. As shown in FIG. 2, the topical administration of Compound A to the cornea (see FIG. 1) of a human subject was found to result in the detection of CPA in the plasma of a human subject, while the IOP of the subject was still declining.

Figure 3:
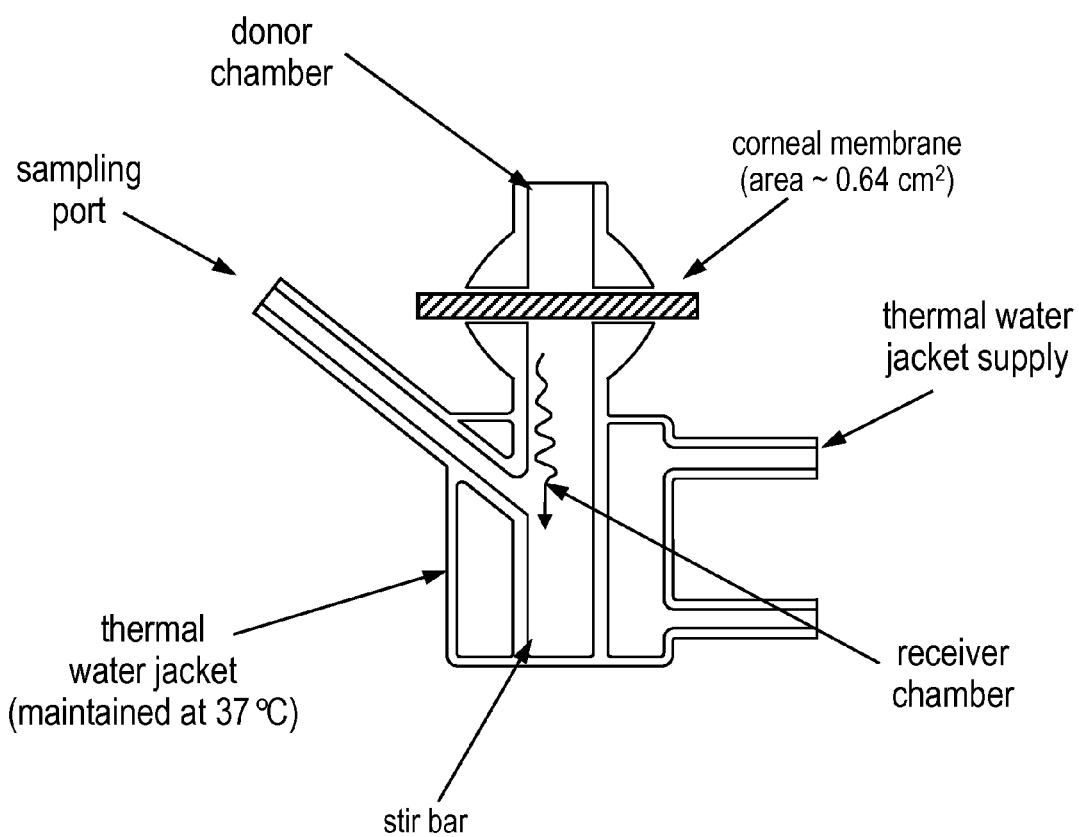
FIG. 3: shows diagrammatically the apparatus employed to determine the in vitro cornea permeability of CPA esters.
Figure 4:
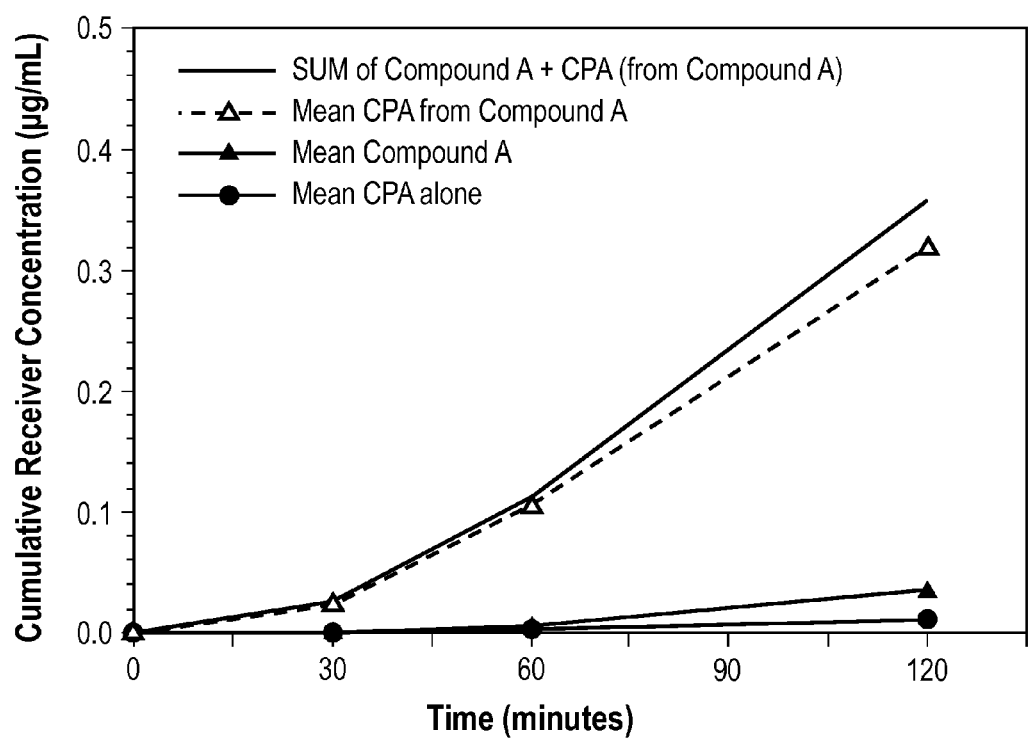
FIG. 4: shows the results from an in vivo study using Dutch Belted rabbits whereby Compound A and CPA alone were administered topically to the cornea of a subject eye of the rabbits and showing the subsequent build up in concentration of CPA in the anterior chamber over time.

To further support the finding that CPA was arising in the plasma of human subject after topical administration of Compound A to the cornea, additional in-vitro animal studies have been completed that show results as seen in FIG. 3 whereby topically applied Compound A to a cornea membrane resulted in the detection of significant levels of CPA on the other side of the cornea membrane. The same model was used to determine the levels of CPA that could be transported across the cornea membrane and the results depicted in FIG. 3 show that the level of CPA transported across the membrane is much less than that detected when Compound A is topically applied to the cornea.

CPA or the compounds according to Formula II can be incorporated into various types of ophthalmic compositions or formulations for delivery. Formula I compounds may be delivered directly to the eye in a cornea-permeable form (for example: topical ocular drops or ointments containing nanoparticles of CPA; or via slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections). It is further contemplated that the agents of the invention may be formulated in intraocular insert or implant devices. It is envisaged that a nonaqueous nanoprecipitation technique could be used to form CPA-loaded nanoparticles having a particle size of less than 0.25 μm (less than 250 nm). The corneal epithelial junction gap has been measured by atomic force microscopy (AFM) as reported in The Use of Atomic Force Microscopy for the Observation of Corneal Epithelium Surface, Tsilimbaris et al., Investigative Ophthalmology & Visual Science, March 2000, Vol. 41, No. 3, pp. 680-686. A technique similar to that described by Dalpiaz et al. in Journal of Pharmaceutical Sciences, 2009, pages 1-13 would be suitable.

Formula II compounds may be delivered directly to the eye in a cornea-permeable form (for example: topical ocular drops or ointments; or via slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections). It is further contemplated that the agents of the invention may be formulated in intraocular insert or implant devices.

The compounds of Formula II are preferably incorporated into topical ophthalmic formulations with a pH of about 4-8 for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity or solubility such as hydroxypropyl β-Cyclodextrin (HPβCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in POAG or OHT patients. Such amounts are referred to herein as "an amount effective to control or reduce IOP, "or more simply" an effective amount." The compounds will normally be contained in these formulations in an amount 0.05 mg/ml to 7.0 mg/ml but preferably in an amount of 0.4 to 7.0 mg/ml. Thus, for topical presentation 1 to 2 drops of these formulations would be delivered to the surface of the eye from 1 to 4 times per day, according to the discretion of a skilled clinician. CPA or the compounds of Formula II can also be used in combination with other glaucoma treatment agents, such as, but not limited to, β-blockers, prostaglandin analogs, prostamides, carbonic anhydrase inhibitors, $α_2$ agonists, miotics, and neuroprotectants, ion channel modulators, $A_1$ agonists, $A_3$ antagonists, $A_2A$ agonists and combinations thereof.

Any reference to a compound of the present invention is therefore to be understood as referring also to the corresponding pro-drugs of the compound of the present invention, as appropriate and expedient.

In a first aspect, the present invention provides a method of reducing intraocular pressure comprising the step of: delivering an effective amount of cyclopentyladenosine according to Formula I to the anterior chamber of an affected eye of a human,

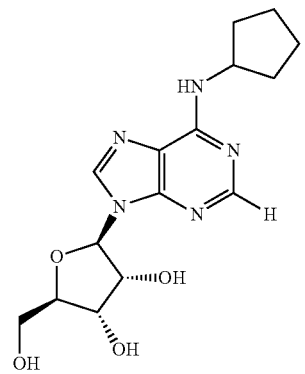 [SMILES: OC[C@H]1O[C@@H](n2cnc3c(NC4CCCC4)ncnc32)[C@H](O)[C@@H]1O]

(I)

with the proviso that the compound of Formula I is not delivered in the form of compound A

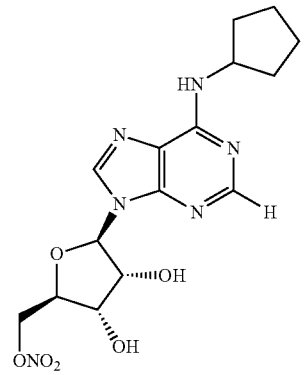

(A)

((2R,3S,4R,5R)-5-(6-(cyclopentylamino)-9H-purin-9-yl)-3,4-dihydroxytetrahydrofuran-2-yl)methyl nitrate.

In one embodiment, the method comprises delivering an effective amount of the compound of Formula I, or a pharmaceutically acceptable salt of, to the anterior chamber of an affected eye of a human.

In another embodiment, the method comprises delivering an effective amount of a pharmaceutical composition comprising the compound of Formula I to the anterior chamber of an affected eye of a human.

In another embodiment, the method comprises delivering an effective amount of a pharmaceutical composition comprising the compound of Formula I, or a pharmaceutically acceptable salt of, to the anterior chamber of an affected eye of a human.

In one embodiment the method comprises the step of applying about 0.05 mg/ml to about 7.0 mg/ml of a compound according to Formula I from 1 to 4 times daily, or in another embodiment the method comprises the step of applying about 20-700 μg of a compound according to Formula I from 1 to 2 times daily or in another embodiment the method comprises the step of applying about 350 μg of a compound according to Formula I from 1 to 2 times daily.

In one embodiment the IOP of the affected eye is reduced by at least 10%. In another embodiment the IOP of the affected eye is reduced by at least 10-20%.

In a further embodiment the IOP of the affected eye is reduced by 20% or more.

In one embodiment the IOP of the affected eye is reduced by at least 10% for more than 3 hours, in another embodiment the IOP of the affected eye is reduced by at least 10-20% for more than 3 hours, in a further embodiment the IOP of the affected eye is reduced by 20% or more for more than 3 hours and in another embodiment the IOP of the affected eye is reduced by at least 10% for at least 6 hours.

In yet another aspect, the present invention provides a method of reducing intraocular pressure comprising the step of: delivering an effective amount of cyclopentyladenosine according to Formula I in a cornea-permeable form to the anterior chamber of an affected eye of a human:

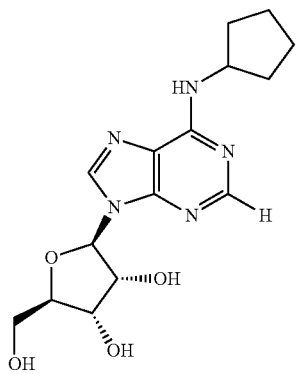

(I)

or a pharmaceutically acceptable salt thereof,
with the proviso that the compound of Formula I is not delivered in the form of compound A

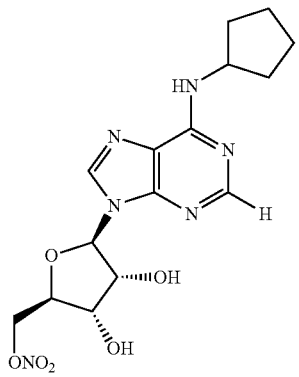

(A)

((2R,3S,4R,5R)-5-(6-(cyclopentylamino)-9H-purin-9-yl)-3,4-dihydroxytetrahydrofuran-2-yl)methyl nitrate.

In one embodiment the method comprises the step of applying about 0.05 mg/ml to about 7.0 mg/ml of a compound according to Formula I from 1 to 4 times daily, or in another embodiment the method comprises the step of applying about 20-700 μg of a compound according to Formula I from 1 to 2 times daily or in another embodiment the method comprises the step of applying about 350 μg of a compound according to Formula I from 1 to 2 times daily.

In one embodiment the IOP of the affected eye is reduced by at least 10%. In another embodiment the IOP of the affected eye is reduced by at least 10-20%.

In a further embodiment the IOP of the affected eye is reduced by 20% or more.

In one embodiment the IOP of the affected eye is reduced by at least 10% for more than 3 hours, in another embodiment the IOP of the affected eye is reduced by at least 10-20% for more than 3 hours, in a further embodiment the IOP of the affected eye is reduced by 20% or more for more than 3 hours and in another embodiment the IOP of the affected eye is reduced by at least 10% for at least 6 hours.

In one embodiment the cornea-permeable form may be achieved by (i) delivering cornea-permeable nanoparticles of CPA.

In one embodiment the cornea-permeable nanoparticles of CPA are less than or about 200 nm.

In another aspect the present invention is directed to a compound of Formula II,

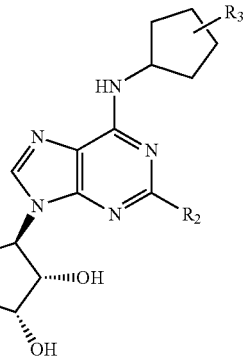

(II)

or a pharmaceutically acceptable salt thereof,
wherein $R_1$ is selected from —(CO)$C_1$-$C_6$ alkyl, —(CO)CH(halo)$_2$, —(CO)phenyl, or a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; or a —(CO)$C_3$-$C_7$ heterocyclic which is optionally substituted with one or more of hydroxy or —(CH$_2$)$_n$OH, where n is 1-6; $R_2$ is selected from —H or halo; and $R_3$ is selected from —H, hydroxy, —O(CO)CH(halo)$_2$, —O(CO)(CH$_2$)$_2$CH$_3$, —O(CO)CH(CH$_3$)$_2$, —O(CO)CH$_2$C(CH$_3$)$_3$.

In another embodiment $R_1$ is selected from —(CO)CH(CH$_3$)$_2$, —(CO)CH$_2$C(CH$_3$)$_3$, —(CO)C(CH$_3$)$_3$, —(CO)(CH$_2$)$_2$CH$_3$, —(CO)CH$_2$CH$_3$, —(CO)phenyl, or a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; or a —(CO)C$_3$-C$_7$ heterocyclic which is optionally substituted with one or more of hydroxy or —(CH$_2$)$_n$OH where n is 1-6; R$_2$ is selected from —H or halo; and R$_3$ is —H.

In one embodiment the compound of Formula II has the following structure:

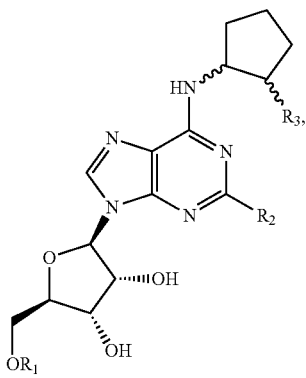

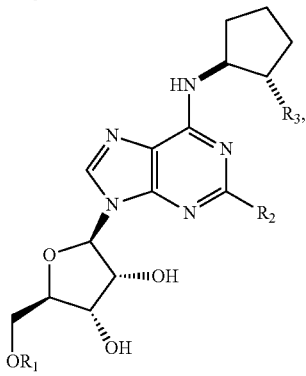

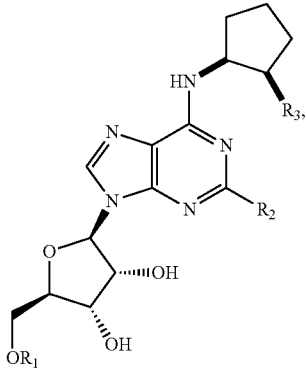

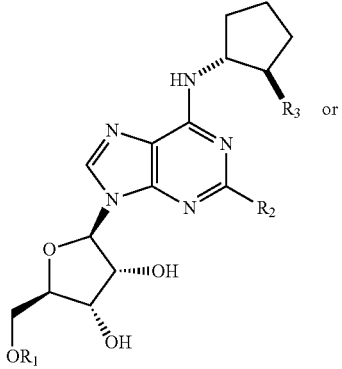

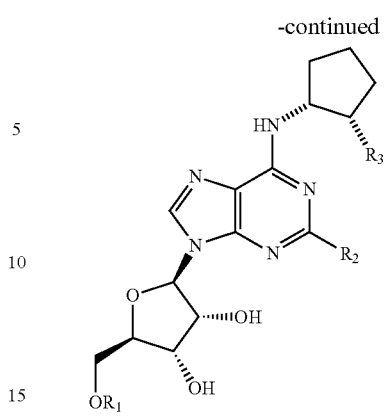

or a pharmaceutically acceptable salt thereof.

In one embodiment the compound of Formula II has the following structure:

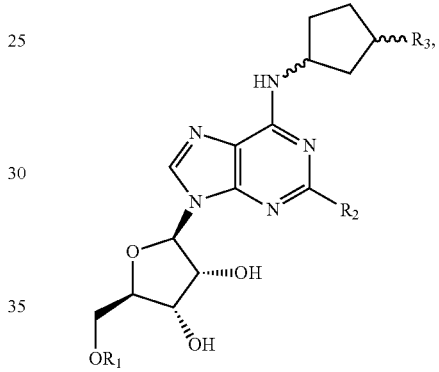

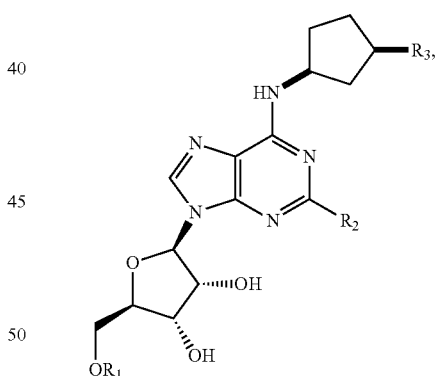

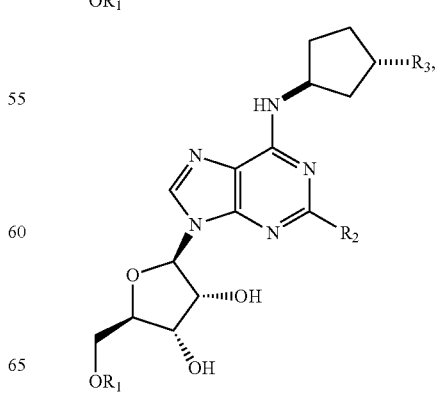

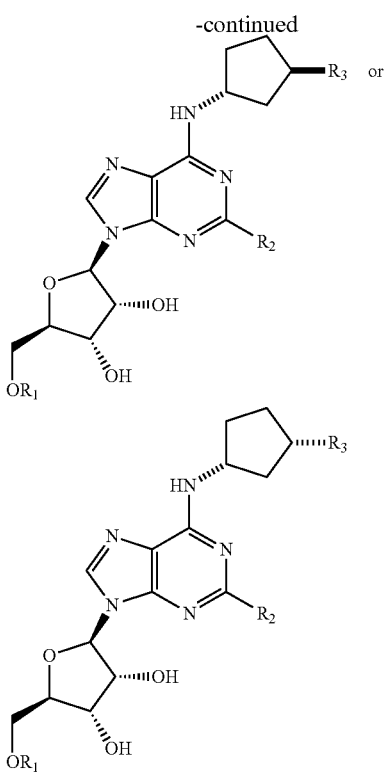

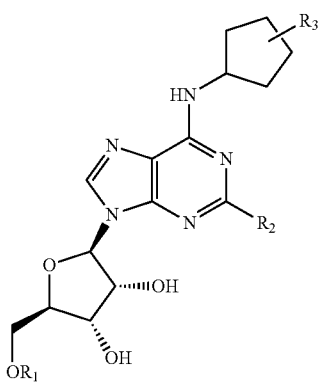

or a pharmaceutically acceptable salt thereof.

In another embodiment $R_1$ is selected from —(CO)CH$(CH_3)_2$ or —(CO)(CH$_2$)$_6$CH$_3$.

In another embodiment $R_2$ is —H.

In still another aspect the invention is directed to a method of reducing IOP and associated diseases and conditions caused by elevated IOP in a human subject by administering an effective amount of a compound of Formula II to an affected eye of the human subject:

(II)

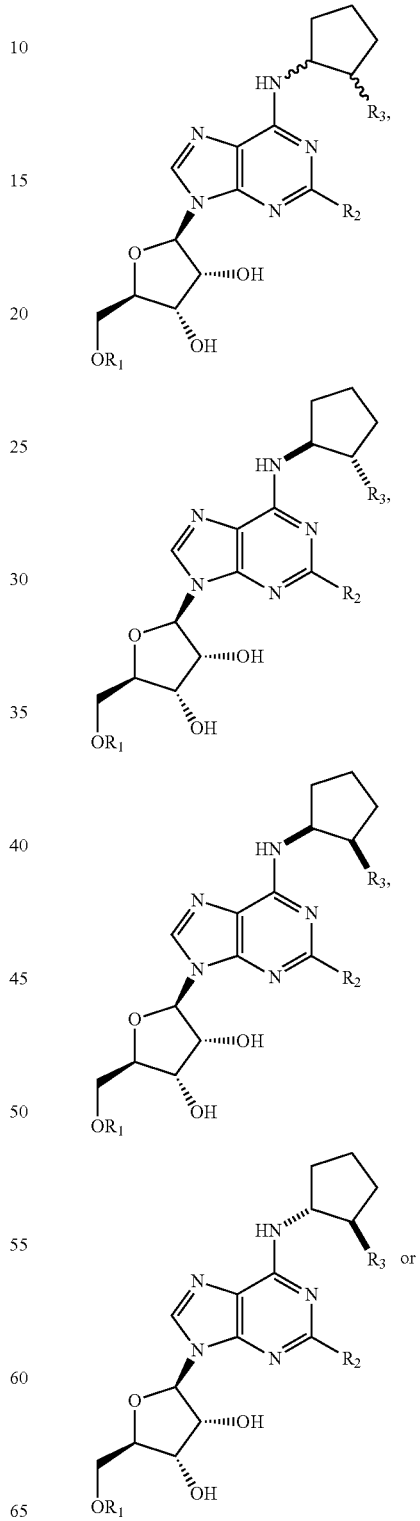

or a pharmaceutically acceptable salt thereof,
wherein $R_1$ is selected from —(CO)C$_1$-C$_6$ alkyl, —(CO)CH(halo)$_2$, —(CO)phenyl, or a —(CO)C$_1$-C$_{10}$ optionally branched aliphatic, —(CO)C$_3$-C$_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; or a —(CO)C$_3$-C$_7$ heterocyclic which is optionally substituted with one or more of hydroxy or —(CH$_2$)$_n$OH where n is 1-6; $R_2$ is selected from —H or halo; and $R_3$ is selected from —H, hydroxy, —O(CO)CH(halo)$_2$, —O(CO)(CH$_2$)$_2$CH$_3$, —O(CO)CH(CH$_3$)$_2$, —O(CO)CH$_2$C(CH$_3$)$_3$.

In one embodiment of the method defined above, the compound of Formula II has the following structure:

21

-continued

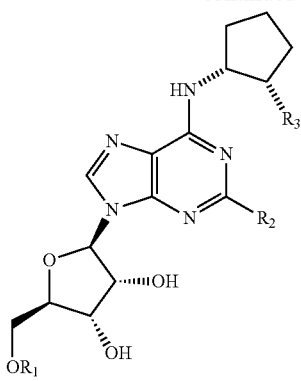

or a pharmaceutically acceptable salt thereof.

In a further embodiment of the method defined above, the compound of Formula II has the following structure:

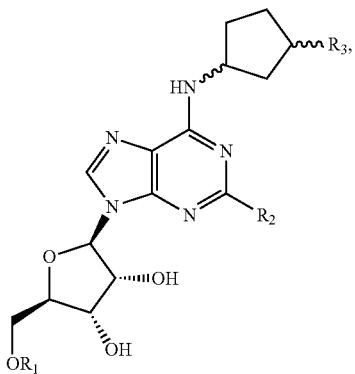

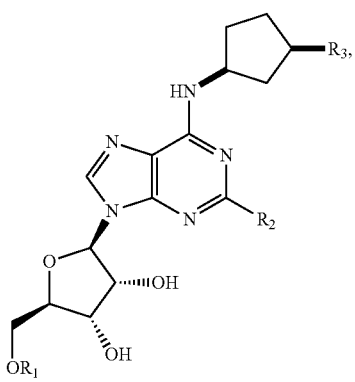

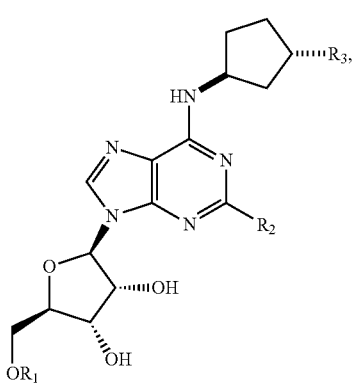

22

-continued

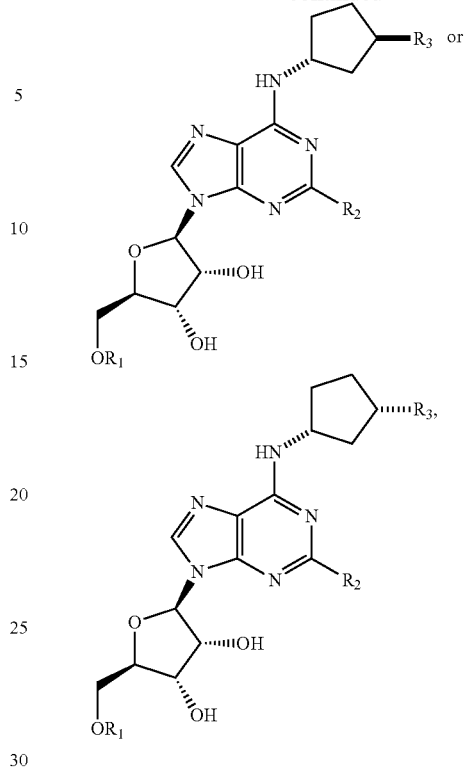

or a pharmaceutically acceptable salt thereof.

In one embodiment $R_1$ is selected from —(CO)CH(CH$_3$)$_2$, —(CO)CH$_2$C(CH$_3$)$_3$, —(CO)C(CH$_3$)$_3$, —(CO)(CH$_2$)$_2$CH$_3$, —(CO)CH$_2$CH$_3$, —(CO)phenyl, or a —(CO)C$_1$-C$_{10}$ optionally branched aliphatic, —(CO)C$_3$-C$_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; or a —(CO)C$_3$-C$_7$ heterocyclic which is optionally substituted with one or more of hydroxy or —(CH$_2$)$_n$OH where n is 1-6; and $R_2$ is selected from —H or halo.

In one embodiment $R_1$ is selected from —(CO)CH(CH$_3$)$_2$, —(CO)(CH$_2$)$_6$CH$_3$, —(CO)CH$_2$C(CH$_3$)$_3$, —(CO)(CH$_2$)$_3$CH$_3$, —(CO)C(CH$_3$)$_3$, —(CO)(CH$_2$)$_2$CH$_3$, —(CO)CH$_2$CH$_3$ or —(CO)phenyl to an affected eye of the subject.

In one embodiment $R_2$ is chloro.

In another embodiment, the compound of Formula II is Compound 2a.

In still another embodiment, the compound of Formula II is Compound 2g.

In one aspect, provided herein is the use of a compound according to Formula I for the manufacture of a medicament for reducing intraocular pressure.

In another aspect, provided herein is the use of a compound according to Formula II for the manufacture of a medicament for the treatment of elevated IOP and diseases and conditions caused by elevated IOP.

In another aspect, provided herein is the use of compound 2a for the manufacture of a medicament for the treatment of elevated IOP and diseases and conditions caused by elevated IOP.

In yet another aspect, provided herein is the use of compound 2g for the manufacture of a medicament for the treatment of elevated IOP and diseases and conditions caused by elevated IOP.

Synthesis

The CPA 5' esters were prepared according to the following procedure shown in Scheme 1 below:

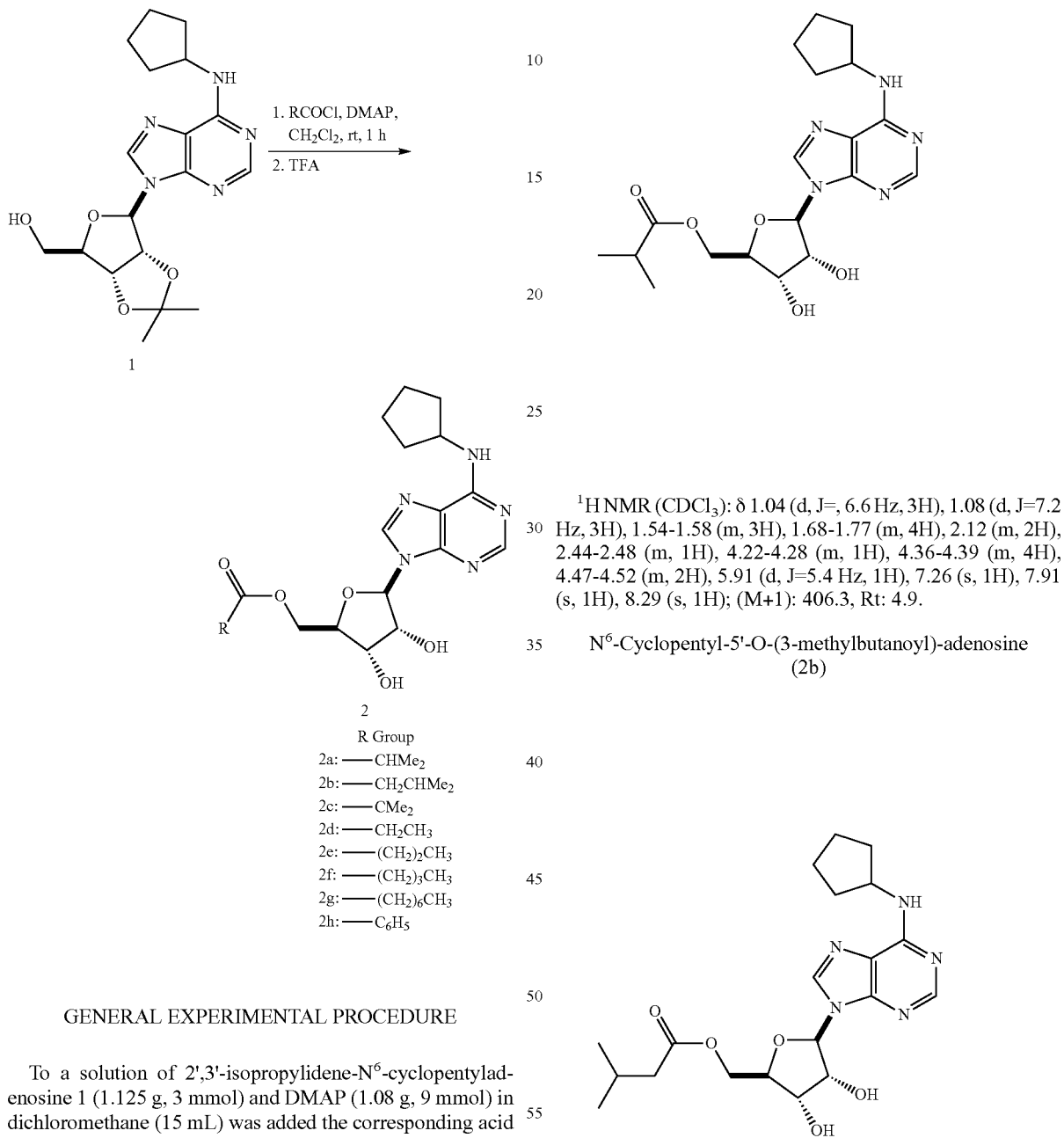

GENERAL EXPERIMENTAL PROCEDURE

To a solution of 2',3'-isopropylidene-$N^6$-cyclopentyladenosine 1 (1.125 g, 3 mmol) and DMAP (1.08 g, 9 mmol) in dichloromethane (15 mL) was added the corresponding acid chlorides drop wise and the reaction mixture was stirred at room temperature for 1 h. The reaction mixture was then diluted with dichloromethane (10 mL) and washed with water (three times) and brine. The organic layer was separated, dried on sodium sulphate and concentrated on rotavaporator. The crude product obtained from the concentration was used as such in next step. A mixture of water (8 mL) and TFA (2 mL) was slowly added to the crude product at 0° C. and then the mixture was stirred at room temperature for 2 h. It was concentrated on rotavaporator and purified on pre-HPLC to get the desired product 2.

$N^6$-Cyclopentyl-5'-O-isobutyryl-adenosine (2a)

$^1$H NMR (CDCl$_3$): δ 1.04 (d, J=, 6.6 Hz, 3H), 1.08 (d, J=7.2 Hz, 3H), 1.54-1.58 (m, 3H), 1.68-1.77 (m, 4H), 2.12 (m, 2H), 2.44-2.48 (m, 1H), 4.22-4.28 (m, 1H), 4.36-4.39 (m, 4H), 4.47-4.52 (m, 2H), 5.91 (d, J=5.4 Hz, 1H), 7.26 (s, 1H), 7.91 (s, 1H), 8.29 (s, 1H); (M+1): 406.3, Rt: 4.9.

$N^6$-Cyclopentyl-5'-O-(3-methylbutanoyl)-adenosine (2b)

$^1$H NMR (CDCl$_3$): δ 0.87 (d, J=, 4.5 Hz, 6H), 1.52-1.50 (m, 3H), 1.68-1.77 (m, 4H), 1.95-2.0 (m, 1H), 2.10 (d, J=6.3 Hz, 4H), 4.22-4.30 (m, 1H), 4.36-4.39 (m, 2H), 4.47-4.52 (m, 2H), 5.93 (d, J=4.8 Hz, 1H), 7.25 (s, 1H), 7.92 (s, 1H), 8.29 (s, 1H).

25

N[6]-Cyclopentyl-5'-O-(2,2-dimethylpropanoyl)-adenosine (2c)

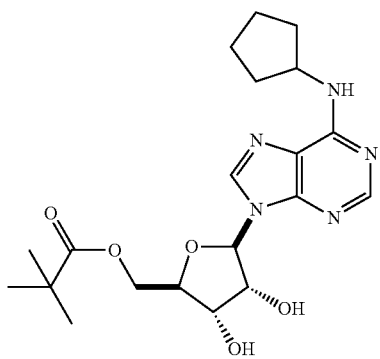

$^1$H NMR (CDCl$_3$): δ 1.09 (s, 9H), 1.52-1.50 (m, 3H), 1.68-1.77 (m, 4H), 2.13 (d, J=5.7 Hz, 3H), 3.64 (s, 1H), 4.22-4.29 (m, 1H), 4.34-4.39 (m, 2H), 4.47-4.52 (m, 2H), 5.93 (d, J=5.7 Hz, 1H), 7.25 (s, 1H), 7.90 (s, 1H), 8.28 (s, 1H).

N[6]-Cyclopentyl-5'-O-propanoyl-adenosine (2d)

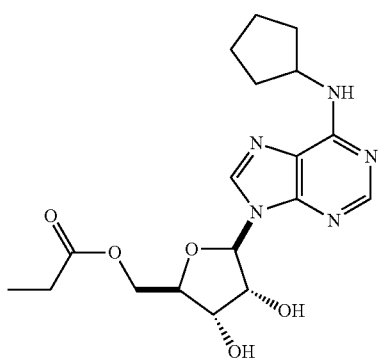

$^1$H NMR (CDCl$_3$): δ 1.05 (t, J=7.5 Hz, 3H), 1.52-1.50 (m, 3H), 1.68-1.77 (m, 4H), 2.13 (d, J=5.7 Hz, 3H), 2.24-2.27 (m, 2H), 3.62 (s, 1H), 4.22-4.29 (m, 1H), 4.34-4.39 (m, 2H), 4.47-4.52 (m, 2H), 4.58 (s, 1H), 5.94 (s, 1H), 7.25 (s, 1H), 7.91 (s, 1H), 8.28 (s, 1H).

26

N[6]-Cyclopentyl-5'-O-butanoyl-adenosine (2e)

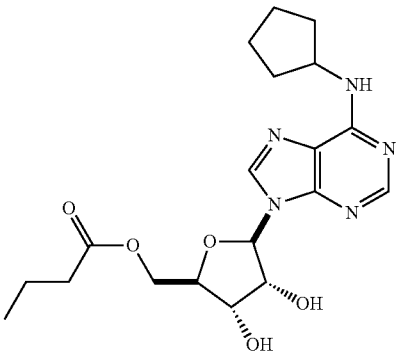

$^1$H NMR (CDCl$_3$): δ 0.86 (t, J=7.2 Hz, 3H), 1.52-1.59 (m, 4H), 1.68-1.77 (m, 4H), 2.11-2.22 (m, 6H), 3.65 (s, 1H), 4.22-4.29 (m, 1H), 4.34-4.39 (m, 2H), 4.47-4.52 (m, 2H), 4.58 (s, 1H), 5.93-5.94 (m, 2H), 7.26 (s, 1H), 7.91 (s, 1H), 8.28 (s, 1H).

N[6]-Cyclopentyl-5'-O-pentanoyl-adenosine (2f)

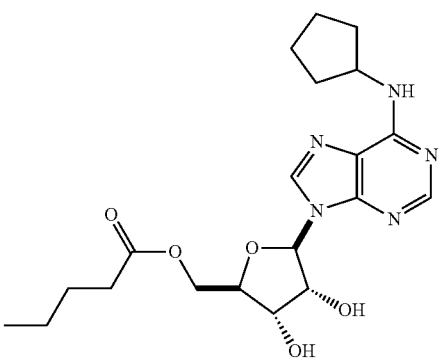

$^1$H NMR (CDCl$_3$): δ 0.81 (t, J=7.2 Hz, 3H), 1.19-1.27 (m, 2H), 1.42-1.58 (m, 6H), 1.68-1.77 (m, 3H), 1.97 (m, 1H), 2.12-2.22 (m, 5H), 3.51 (s, 1H), 4.22-4.29 (m, 1H), 4.34-4.39 (m, 2H), 4.47-4.52 (m, 2H), 4.59 (s, 1H), 5.92 (d, J=5.4 Hz, 2H), 7.26 (s, 1H), 7.90 (s, 1H), 8.29 (s, 1H).

27
N⁶-Cyclopentyl-5'-O-octanoyl-adenosine (2g)
28
N⁶-Cyclopentyl-5'-O-benzoyl-adenosine (2h)
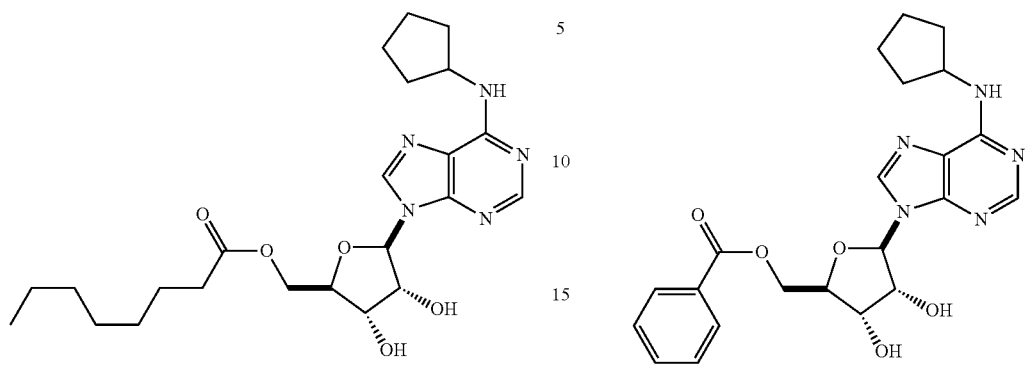
¹H NMR (CDCl₃): δ 0.83-0/87 (m, 3H), 1.19-1.30 (m, 9H), 1.46-1.79 (m, 6H), 2.10-2.22 (m, 3H), 2.34 (dd, J=7.2 and 7.5 Hz, 1H), 4.22-4.29 (m, 1H), 4.34-4.39 (m, 2H), 4.46-4.52 (m, 2H), 4.59 (s, 1H), 5.92 (d, J=5.4 Hz, 2H), 7.26 (s, 1H), 7.93 (s, 1H), 8.30 (s, 1H), (M+1): 462.3.
¹H NMR (CDCl₃): δ 1.52-1.58 (m, 2H), 1.68-1.76 (m, 3H), 2.10-2.20 (m, 3H), 3.7 (s, 1H), 4.49-4.54 (m, 2H), 4.60-4.65 (m, 4H), 5.94 (d, J=4.8 Hz, 2H), 7.25-7.33 (m, 3H), 7.46-7.49 (m, 1H), 7.81 (d, J=6.9 Hz, 2H), 7.89 (s, 1H), 8.24 (s, 1H)
The N⁶ hydroxy or N⁶ esters substituted CPA esters were prepared according to the procedure shown in Scheme 2 below:
Scheme 2
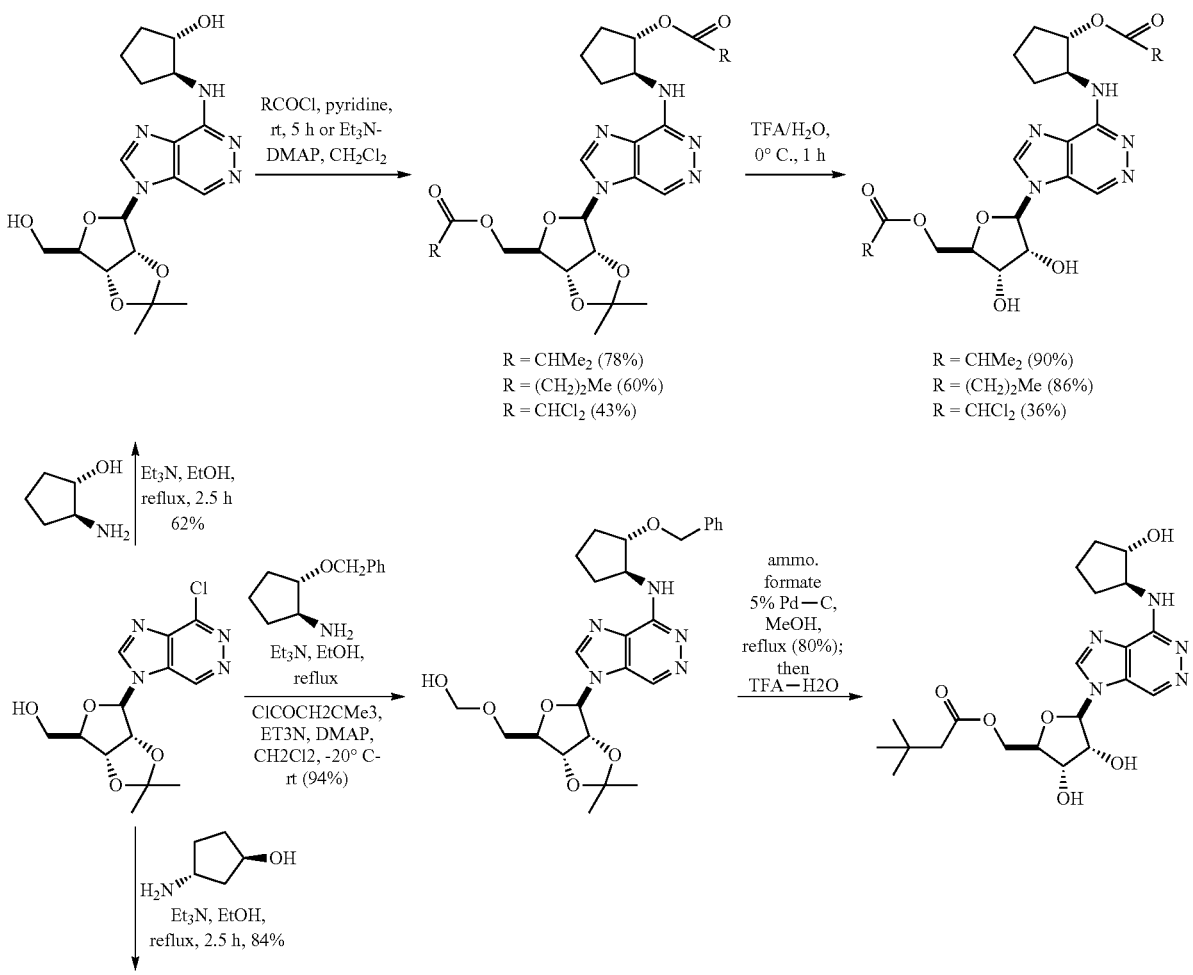

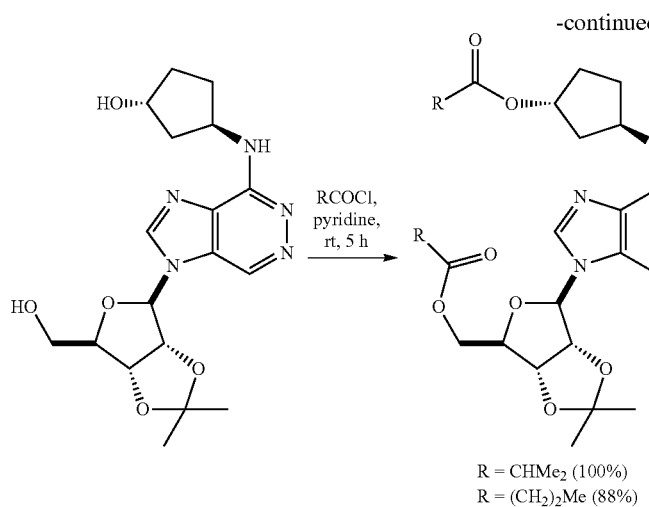

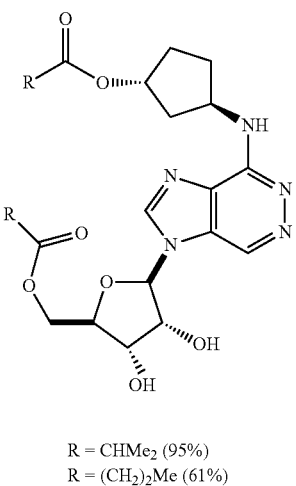

R = CHMe₂ (100%)
R = (CH₂)₂Me (88%)

R = CHMe₂ (95%)
R = (CH₂)₂Me (61%)

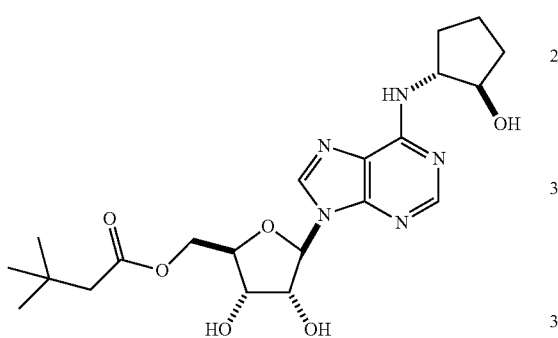

((2R,3S,4R,5R)-3,4-Dihydroxy-5-(6-((1R,2R)-2-hydroxycyclopentylamino)-9H-purin-9-yl)tetrahydrofuran-2-yl)methyl 3,3-dimethylbutanoate (3a)

¹HNMR (DMSO-d6): 0.80-0.84 (m, 1H), 0.89 (s, 9H), 1.42-1.65 (m, 3H), 1.80-2.02 (m, 3H), 3.14 (s, 2H), 4.01-4.27 (m, 4H), 4.66 (s, 1H), 4.86 (s, 1H), 5.38 (s, 1H), 5.58 (s, 1H), 5.88 (d, J=5.1 Hz, 1H), 7.24 (bs, 1H), 7.67 (d, J=6.6 Hz, 1H), 8.18 (s, 1H), 8.28 (s, 1H).

((2R,3S,4R,5R)-5-(6-((1R,2R)-2-(2,2-Dichloroacetoxy)cyclopentylamino)-9H-purin-9-yl)-3,4-dihydroxytetrahydrofuran-2-yl)methyl 2,2-dichloroacetate (3b)

¹HNMR (DMSO-d6): 0.80-0.84 (m, 1H), 1.07-1.12 (m, 2H), 1.64-1.20 (m, 2H), 2.10-2.13 (m, 2H), 4.13 (s, 1H), 4.24 (s, 1H), 4.40-4.62 (m, 3H), 5.26 (s, 1H), 5.43 (s, 1H), 5.60 (d, J=4.8 Hz, 1H), 5.92 (d, J=4.8 Hz, 1H), 6.82 (s, 1H), 6.90 (s, 1H), 8.05 (s, 1H), 8.19 (s, 1H), 8.31 (s, 1H).

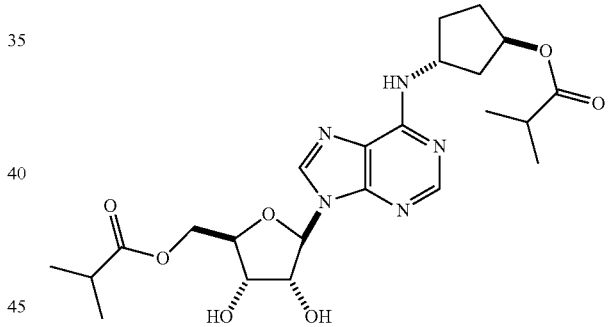

((2R,3S,4R,5R)-3,4-Dihydroxy-5-(6-((1R,3R)-3-(isobutyryloxy)cyclopentylamino)-9H-purin-9-yl)tetrahydrofuran-2-yl)methyl isobutyrate (3c)

MS (ES⁺): m/z 392.2 (M+1)

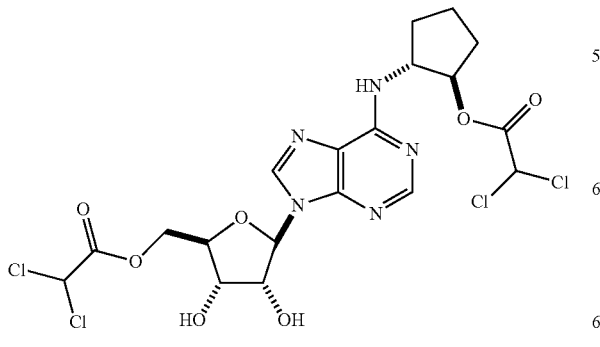

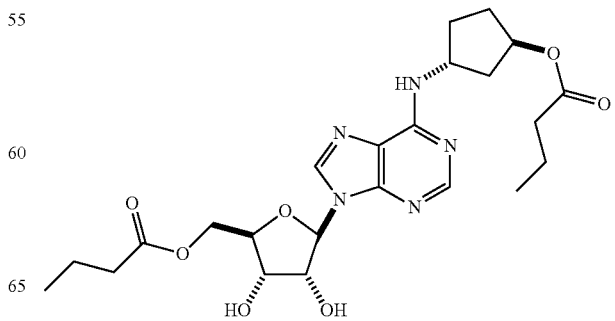

31

((2R,3S,4R,5R)-5-(6-((1R,3R)-3-(Butyryloxy)cyclo-pentylamino)-9H-purin-9-yl)-3,4-dihydroxytetrahy-drofuran-2-yl)methyl butyrate (3d)

MS (ES⁺): m/z 392.2 (M+1)

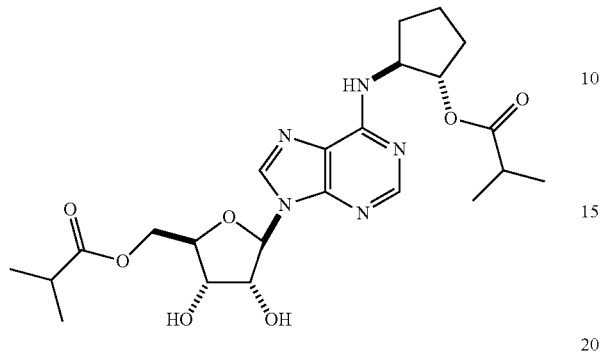

((2R,3S,4R,5R)-3,4-dihydroxy-5-(6-((1S,2S)-2-(Isobutyryloxy)cyclopentylamino)-9H-purin-9-yl)tetrahydrofuran-2-yl)methyl isobutyrate (3e)

MS (ES⁺) m/z 392.2 (M+1)

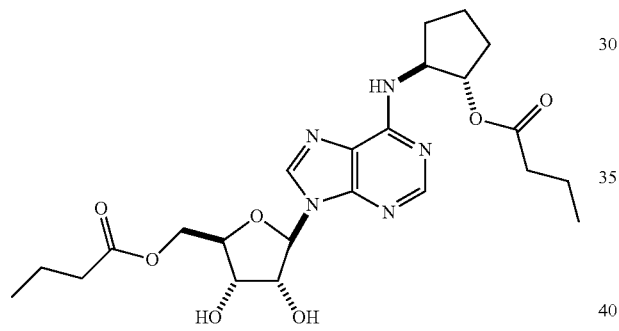

((2R,3S,4R,5R)-5-(6-((1S,2S)-2-(Butyryloxy)cyclo-pentylamino)-9H-purin-9-yl)-3,4-dihydroxytetrahy-drofuran-2-yl)methyl butyrate (3f)

MS (ES⁺) m/z 392.2 (M+1)

The 2'3' esters defined above could be made according to the following general procedure.

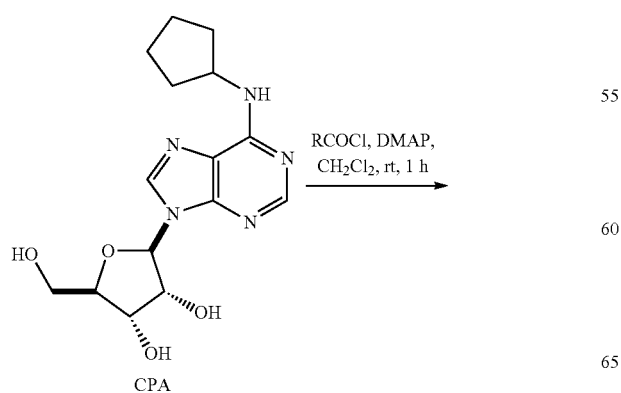

32

-continued

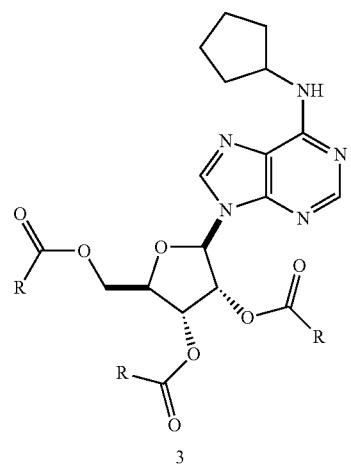

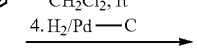

Example I

In-Vitro Cornea Permeability Studies

With reference to FIG. 3, which shows an in-vitro system for measuring the cornea permeability of a cornea the compounds 2a and 2g were selected for study using dutch belted cornea membranes.

The compounds (2a) and (2g) were prepared in powder form by Inotek Pharmaceuticals Corp. (Lexington, Mass.). Low-permeability control compound atenolol and all other chemicals were purchased from Sigma (St. Louis, Mo.). The buffer used in the permeability assessment was a glutathione-bicarbonated Ringer's (GBR) solution (110 mM NaCl, 5 mM KCl, 1 mM NaH2PO4, 30 mM NaHCO$_3$, 1 mM CaCl$_2$, 0.75 mM Mg Cl$_2$, 5 mM D-glucose, and 0.3 mM reduced glutathione), pH 7.4, which was freshly prepared on the day of the experiment and oxygenated with O$_2$/CO$_2$ (95:5) to pH 7.4.

The compounds (2a) and (2g) were reconstituted in saline and diluted (10-fold) into the assay at a final concentration between 50 µM and 2.6 mM. Male Dutch-belted pigmented rabbits (1.5-2.5 kg body weight, 3-3.5 months old) were purchased from Covance Research Products Inc. (Denver, Pa.). The animal handling performed in this study conformed to the Guiding Principles in the Care and Use of Animals (DHEW Publication, NIH 80-23). The rabbits were euthanized by CO$_2$ asphyxiation, and the heads were transported on ice to a testing facility, where dissection of the eyes was performed.

The corneal tissues were excised and mounted on a Harvard vertical diffusion apparatus as shown in FIG. 3 with a diffusion area of 0.64 cm2. Preheated (37° C.), pH 7.4, GBR buffer was added to the mucosal (1.5 mL) and the serosal (1.5 mL) chambers. The diffusion apparatus was maintained at 37° C. throughout the entire transport experiment. Oxygenation and agitation were achieved by bubbling O$_2$/CO$_2$ (95:5) through each chamber at a rate of 5-6 bubbles per second. After the 30-minute equilibration, blank GBR buffer in the mucosal (donor) chamber was withdrawn and replaced with GBR assay buffer containing the compound (2a) or the compound (2g). The transport experiments lasted 2 hours and were performed in duplicate. Every 60 minutes, 0.2-mL samples were collected from the serosal (receiver) chamber and replenished with 0.2-mL blank GBR buffer, except at the last time point; at the end of the experiment, samples were also collected from the mucosal (donor) chambers for mass balance determination.

After the transport experiment, tissue integrity (system suitability) was assessed by measuring the permeation of a low permeability control compound, atenolol, across the tissue. Donor chamber contents were replaced with GBR buffer containing 100 µM atenolol, and receiver chambers were replaced with fresh blank GBR buffer. After 30 minutes of incubation, samples were collected from both chambers for analysis. The post-experimental system suitability assessment was considered acceptable if duplicate measurements yielded a mean apparent permeability ($P_{app}$) value for atenolol <1·10$^{-6}$ cm/s.

Compound A and compounds (2a) and (2g) and atenolol concentrations in the donor and receiver chambers were analyzed by LC-MS/MS methods. Apparent permeability (Papp) values were calculated using the following equation:

$$P_{app} = (dC_r/dt) \cdot V_r / (A \cdot C_0)$$

Where, dCr/dt was the slope of the linear portion of the cumulative concentration in the receiver compartment over time in µM/sec, $V_r$ was the volume of the receiver chamber in cm$^3$, A was the diffusion area in cm$^2$, and $C_0$ was the measured dosing concentration in µM.

Recovery was calculated using the following equation:

$$\text{Recovery} = 100 \cdot (V_r \cdot C_r^{final} + V_d \cdot C_d^{final}) / (V_d \cdot C_0)$$

Where, $V_r$ was the volume of the receiver compartment in cm$^3$, $V_d$ was the volume of the donor compartment in cm$^3$, $C_0$ was the dosing concentration in µM, $C_r^{final}$ was the cumulative receiver concentration in µM, and $C_d^{final}$ was the donor concentration in µM at the end of the incubation.

Figure 5:
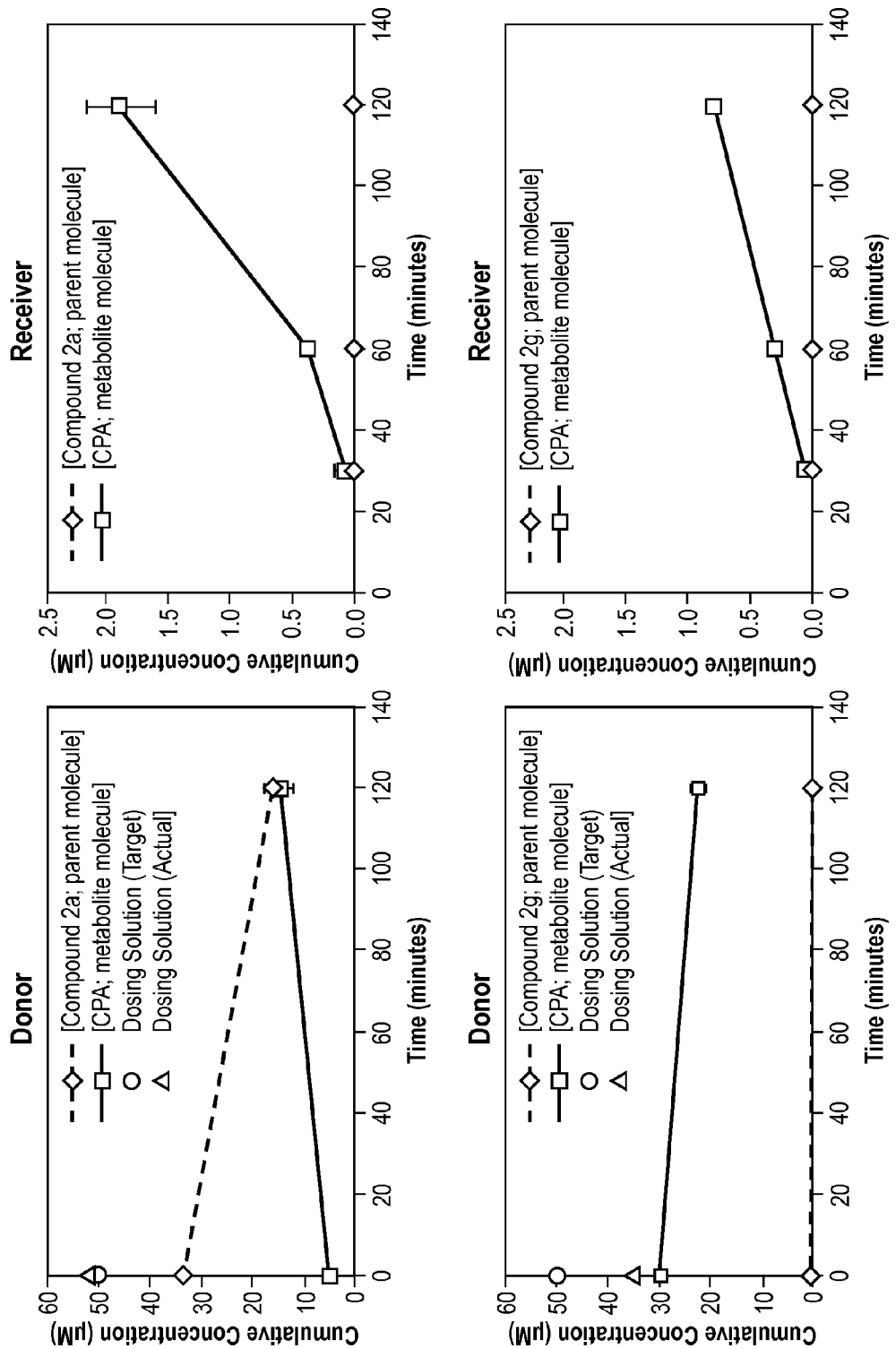
FIG. 5: shows the results of an in vitro cornea permeability study showing the significant cornea permeability of CPA esters (Compound 2a and Compound 2g) respectively.

It can be seen from the graphs shown in FIG. 5 that significant levels of CPA were measureable when Compounds (2a) and (2g) were placed in the donor chamber, providing support for the release of CPA from Compounds (2a) and (2g) after passage through a cornea membrane.

Example II

Analysis of Human Plasma after Administration of Compound A

After the administration of Compound A topically to a cornea of a human, at selected time points (e.g., Day 1: pre-dose, 5, 15, 25, 35, and 45 min and 1, 2, 4, 8 and 24 hours) samples of whole blood (10 mL) were collected for pharmacokinetic assessments using a vacutainer tube containing sodium heparin as an anticoagulant, via catheter, saline lock, or by venipuncture. The blood components were separated by centrifugation at 4° C. following standard clinical laboratory procedures for preparation of plasma from whole blood (e.g., 3000 rpm for approximately 10 min). For each sample, approximately 1 mL of plasma was stored at −20° C. or colder until analysis for Compound A and CPA concentration. Human plasma samples were analyzed for Compound A concentrations using a validated liquid chromatography/tandem mass spectrometry (LC/MS/MS) method with a lower limit of quantitation (LLOQ) of 10.0 pg/mL and a linear range from 10.0 to 2000 pg/mL. Plasma concentrations of (N(6)-cyclopentyladenosine, CPA) were also measured in some samples using a validated LC/MS/MS method with a lower limit of quantitation of 10.0 pg/mL and a linear range from 10.0 to 2000 pg/mL.

As a result of this analysis, CPA has been identified as an active metabolite in clinical studies after the topical administration of Compound A to the cornea of human subjects. The IOP of the human subjects continues to decline after the buildup of CPA in the plasma of the human subjects and that no transient elevation in IOP is seen suggesting that the selectivity of CPA over the $A_2$ and $A_3$ adenosine receptors is significant enough to avoid any transient increase in IOP. As shown in FIG. 2, the topical administration of Compound A to the cornea (see FIG. 1) of a human subject was found to result in the detection of CPA in the plasma of a human subject, while the IOP of the subject was still declining.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized

The invention claimed is:

1. A compound of Formula II

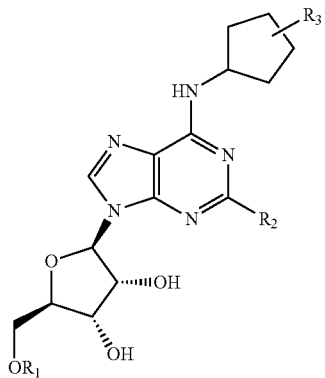

(II)

or a pharmaceutically acceptable salt thereof, wherein $R_1$ is selected from —(CO)$C_1$-$C_6$ alkyl, —(CO)CH(halo)$_2$, —(CO)phenyl, a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; and a —(CO)$C_3$-$C_7$ heterocyclyl which is optionally substituted with one or more of hydroxy or —(CH$_2$)$_n$OH, wherein n is 1-6; $R_2$ is selected from —H and halo; and $R_3$ is selected from hydroxy, —O(CO)CH(halo)$_2$, —O(CO)(CH$_2$)$_2$CH$_3$, —O(CO)CH(CH$_3$)$_2$, and —O(CO)CH$_2$C(CH$_3$)$_3$.

2. The compound of Formula II, as claimed in claim 1, having the structure:

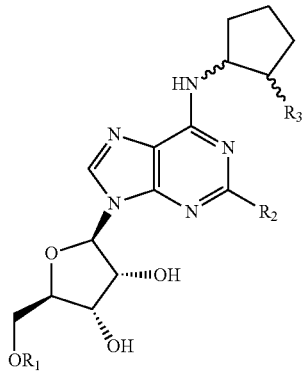

or a pharmaceutically acceptable salt thereof.

3. The compound of Formula II, as claimed in claim 2, having a structure selected from:

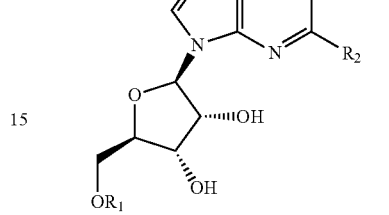

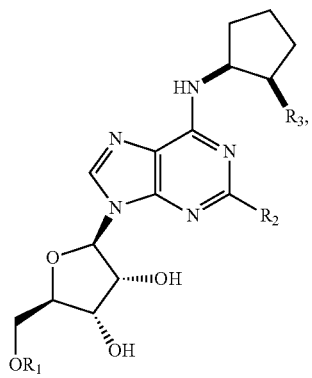

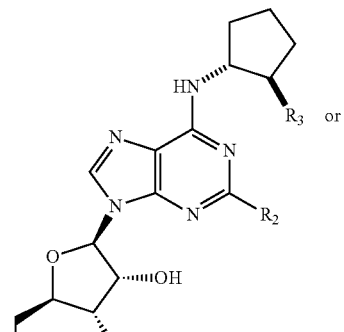

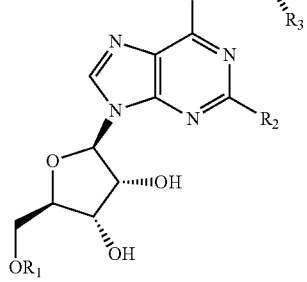

or a pharmaceutically acceptable salt thereof.

4. The compound of Formula II, as claimed in claim 1, having the structure:

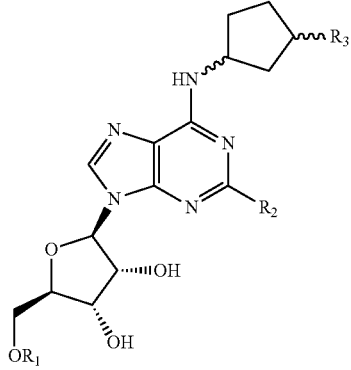

or a pharmaceutically acceptable salt thereof.

5. The compound of Formula II as claimed in claim 4, having the structure:

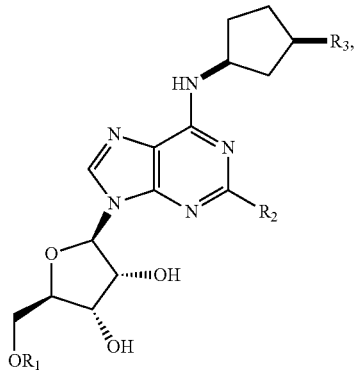

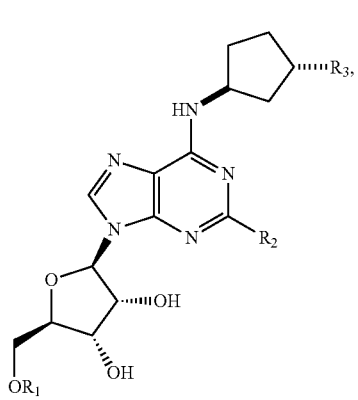

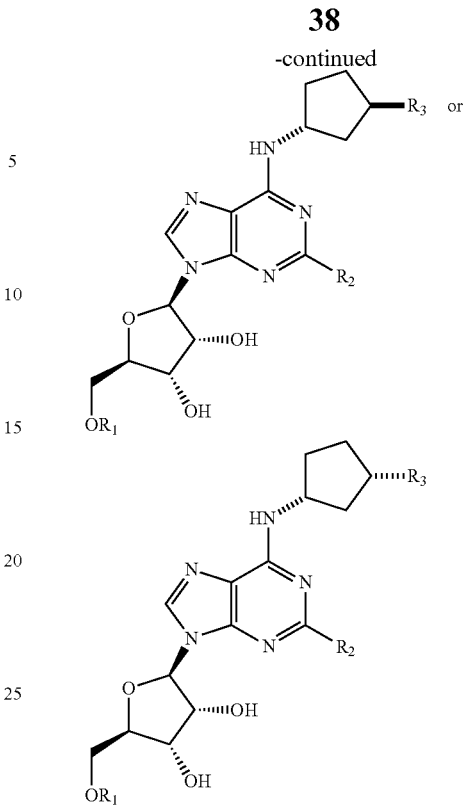

or a pharmaceutically acceptable salt thereof.

6. The compound of claim 1, wherein $R_1$ is selected from —(CO)CH(CH$_3$)$_2$, —(CO)CH$_2$C(CH$_3$)$_3$, —(CO)C(CH$_3$)$_3$, —(CO)(CH$_2$)$_2$CH$_3$, —(CO)CH$_2$CH$_3$, —(CO)phenyl, a —(CO)C$_1$-C$_{10}$ optionally branched aliphatic, —(CO)C$_3$-C$_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; and a —(CO)C$_3$-C$_7$ heterocyclyl which is optionally substituted with one or more of hydroxy or —(CH$_2$)$_n$OH where n is 1-6; and $R_2$ is selected from —H and halo.

7. The compound of claim 1, wherein $R_1$ is selected from —(CO)CH(CH$_3$)$_2$ or —(CO)(CH$_2$)$_6$CH$_3$.

8. The compound of claim 1, wherein $R_2$ is —H.

9. A compound of the formula 2a:

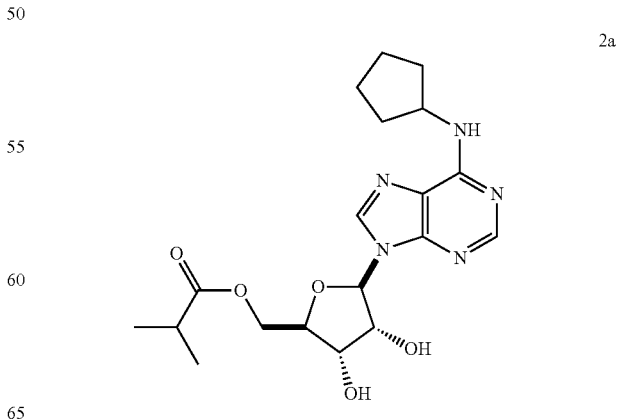

or a pharmaceutically acceptable salt thereof.

10. A compound selected from the group consisting of formula 2b, 2c and 2h:

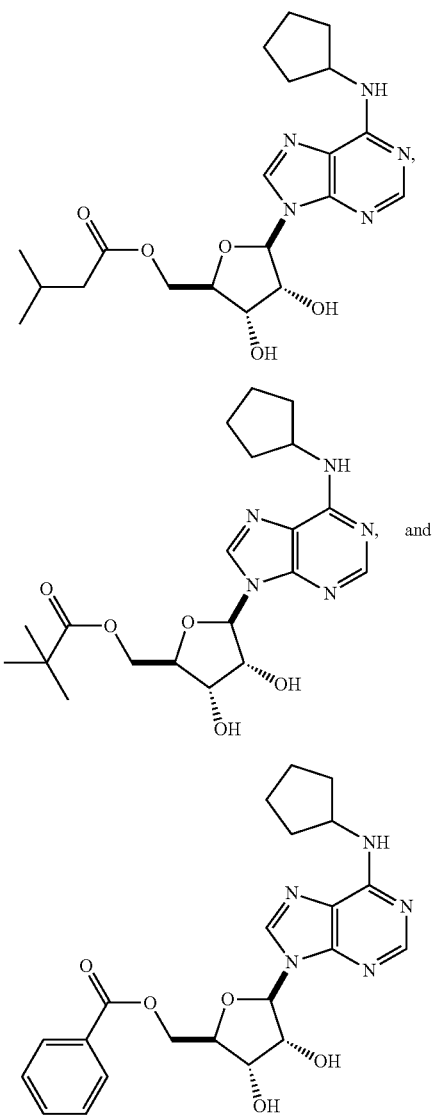

or a pharmaceutically acceptable salt thereof.

11. An ophthalmic pharmaceutical composition comprising a compound of Formula II

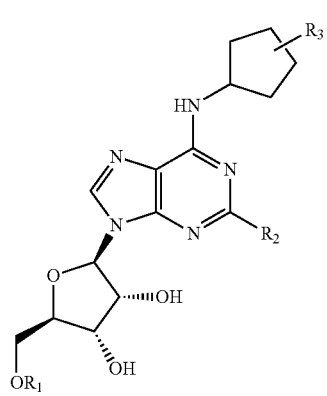

or a pharmaceutically acceptable salt thereof,
wherein $R_1$ is selected from —(CO)$C_1$-$C_6$ alkyl, —(CO)CH(halo)$_2$, —(CO)phenyl, and a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; and a —(CO)$C_3$-$C_7$ heterocyclyl heterocyclic which is optionally substituted with one or more of hydroxy or —(CH$_2$)$_n$OH, wherein n is 1-6; $R_2$ is selected from —H and halo; and $R_3$ is selected from hydroxy, —O(CO)CH(halo)$_2$, —O(CO)(CH$_2$)$_2$CH$_3$, —O(CO)CH(CH$_3$)$_2$, and —O(CO)CH$_2$C(CH$_3$)$_3$, and a pharmaceutically acceptable carrier.

12. An ophthalmic pharmaceutical composition comprising compound 2a

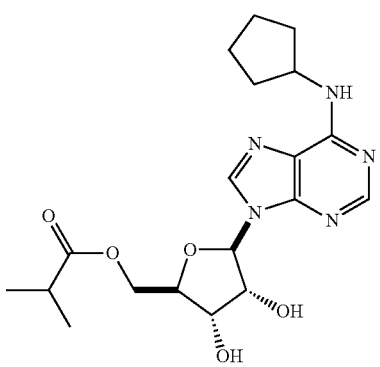

or a pharmaceutically acceptable salt thereof, and a pharmaceutically acceptable carrier.

13. An ophthalmic pharmaceutical composition comprising a compound selected from the group consisting of compound 2b, compound 2c and compound 2h:

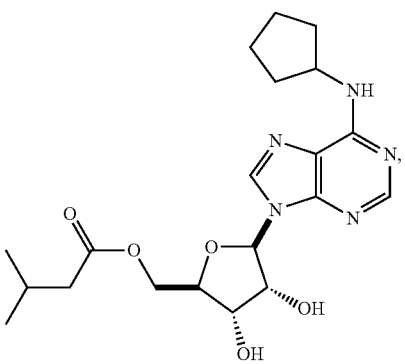

-continued

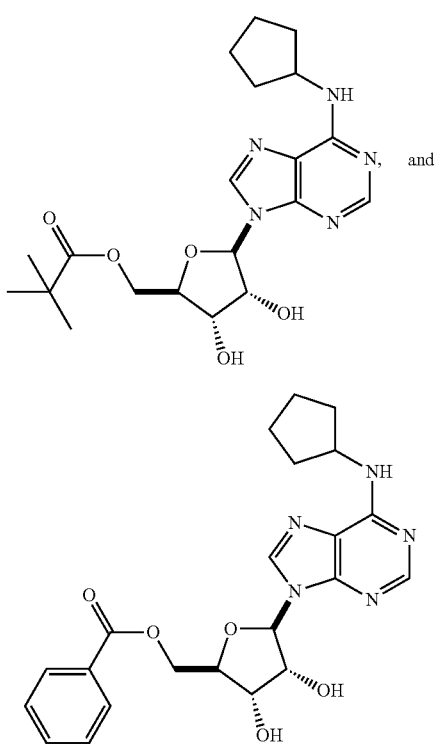

2c

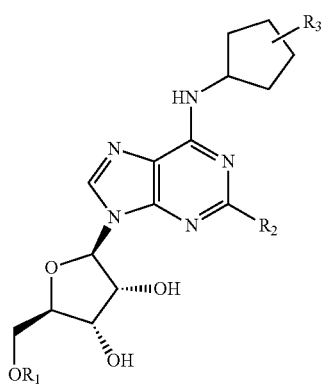

2h or a pharmaceutically acceptable salt thereof, and a pharmaceutically acceptable carrier.

14. A method of reducing intraocular pressure (IOP) in a human subject in need thereof by administering an effective amount of a compound of Formula II, or a pharmaceutically acceptable salt thereof, to an affected eye of the human subject, (II)

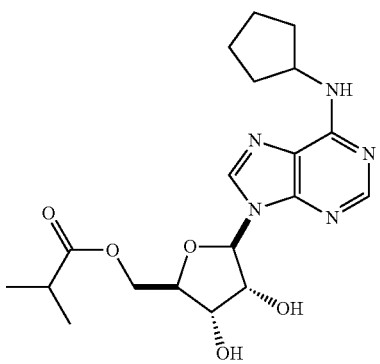

wherein $R_1$ is selected from —(CO)$C_1$-$C_6$ alkyl, —(CO)CH(halo)$_2$, —(CO)phenyl, and a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; and a —(CO)$C_3$-$C_7$ heterocyclyl which is optionally substituted with one or more of hydroxy or —(CH$_2$)$_n$OH, wherein n is 1-6; $R_2$ is selected from —H and halo; and $R_3$ is selected from hydroxy, —O(CO)CH(halo)$_2$, —O(CO)(CH$_2$)$_2$CH$_3$, —O(CO)CH(CH$_3$)$_2$, and —O(CO)CH$_2$C(CH$_3$)$_3$.

15. A method of reducing IOP in a human subject in need thereof by administering an effective amount of Compound 2a, 2a

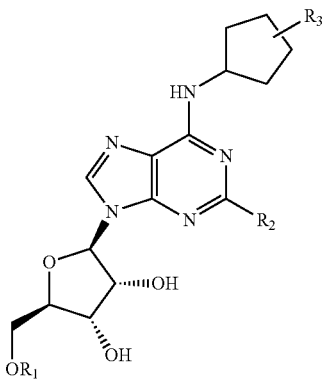

or a pharmaceutically acceptable salt thereof, to an affected eye of the human subject.

16. A method of treating diseases and conditions caused by elevated IOP in a human subject in need thereof by administering an effective amount of a compound of Formula II, or a pharmaceutically acceptable salt thereof, to an affected eye of the human subject, (II)

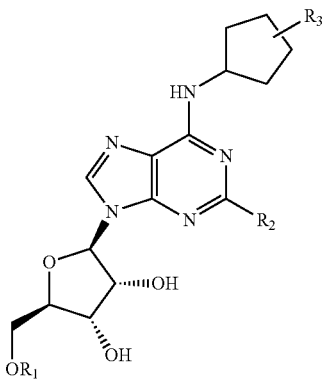

wherein $R_1$ is selected from —(CO)$C_1$-$C_6$ alkyl, —(CO)CH(halo)$_2$, —(CO)phenyl, and a —(CO)$C_1$-$C_{10}$ optionally branched aliphatic, —(CO)$C_3$-$C_8$ cycloalkyl which is optionally substituted with one or more of hydroxy or —(CH$_2$)$_n$OH where n is 1-6, —(CO)aryl which is optionally substituted with one or more of hydroxy or —(CH$_2$)$_n$OH where n is 1-6; and a —(CO)$C_3$-$C_7$ heterocyclyl which is optionally substituted with one or more of hydroxy or —(CH$_2$)$_n$OH, wherein n is 1-6; $R_2$ is selected from —H and halo; and $R_3$ is selected from hydroxy, —O(CO)CH(halo)$_2$, —O(CO)(CH$_2$)$_2$CH$_3$, —O(CO)CH(CH$_3$)$_2$, and —O(CO)CH$_2$C(CH$_3$)$_3$.

17. A method of treating diseases and conditions caused by elevated IOP in a human subject in need thereof by administering an effective amount of Compound 2a,

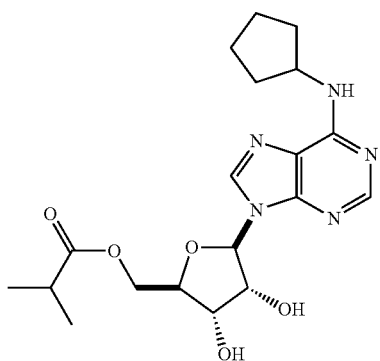

2a or a pharmaceutically acceptable salt thereof, to an affected eye of the human subject.

18. A method of reducing IOP in a human subject in need thereof by administering an effective amount of a compound selected from the group consisting of compound 2b, compound 2c and compound 2h:

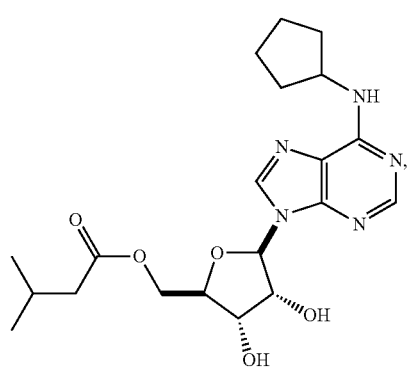

2b

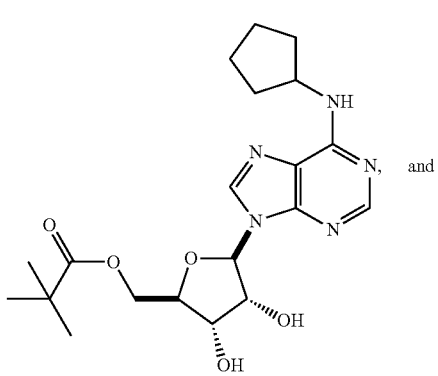

2c

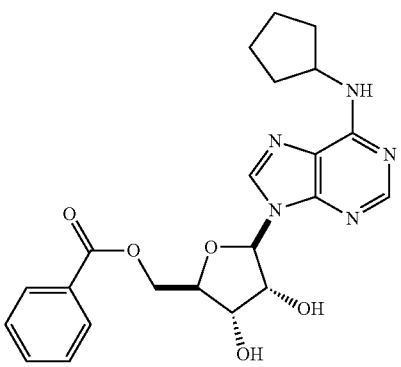

2h or a pharmaceutically acceptable salt thereof, to an affected eye of the human subject.

19. A method of treating diseases and conditions caused by elevated IOP in a human subject in need thereof by administering an effective amount of a compound selected from the group consisting of compound 2b, compound 2c and compound 2h:

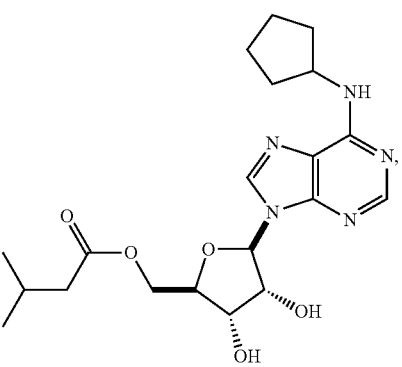

2b

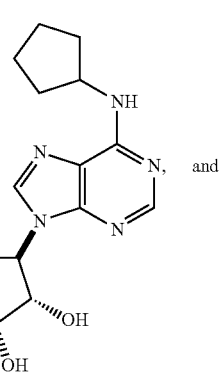

2c and

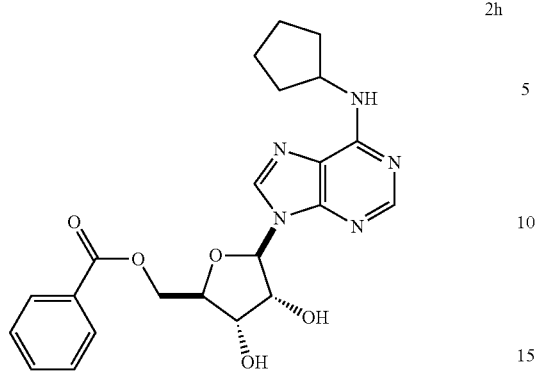
2h
or a pharmaceutically acceptable salt thereof, to an affected eye of the human subject.
* * * * *

UNITED STATES PATENT AND TRADEMARK OFFICE
CERTIFICATE OF CORRECTION

PATENT NO. : 8,476,247 B2
APPLICATION NO. : 13/072349
DATED : July 2, 2013
INVENTOR(S) : Norman N. Kim et al.

Page 1 of 1

It is certified that error appears in the above-identified patent and that said Letters Patent is hereby corrected as shown below:

In the Claims

Claim 3, column 36, line 40, delete "or" and insert --and--

Claim 11, column 40, line 3, delete "and"

Claim 11, column 40, line 10, delete "heterocyclic"

Claim 14, column 41, line 59, delete "and"

Claim 15, column 42, line 53, delete "and"

Signed and Sealed this
Twenty-first Day of October, 2014

Michelle K. Lee
*Deputy Director of the United States Patent and Trademark Office*